US008249714B1

(12) United States Patent
Hartman et al.

(10) Patent No.: US 8,249,714 B1
(45) Date of Patent: Aug. 21, 2012

(54) LOWER EXTREMITY EXERCISE DEVICE WITH STIMULATION AND RELATED METHODS

(75) Inventors: Eric Hartman, Versailles, KY (US); James Abbas, Scottsdale, AZ (US); JoAnne Resig, Lexington, KY (US); John Alton, Lexington, KY (US); Mark Griffin, Louisville, KY (US); Nancy Quick, Saco, ME (US)

(73) Assignee: Customkynetics, Inc., Versailles, KY (US)

( * ) Notice: Subject to any disclaimer, the term of this patent is extended or adjusted under 35 U.S.C. 154(b) by 1111 days.

(21) Appl. No.: 11/483,786

(22) Filed: Jul. 10, 2006

Related U.S. Application Data

(60) Provisional application No. 60/697,772, filed on Jul. 8, 2005.

(51) Int. Cl.
*A61N 1/18* (2006.01)
(52) U.S. Cl. ........................................................ 607/48
(58) Field of Classification Search .................. 601/21, 601/23, 24, 34–36; 128/905; 607/48; 482/148
See application file for complete search history.

(56) References Cited

U.S. PATENT DOCUMENTS

| | | | |
|---|---|---|---|
| 3,083,712 A | 4/1963 | Keegan, Jr. | |
| 3,589,358 A | 6/1971 | Megal | |
| 3,741,200 A | 6/1973 | Morin | |
| 4,113,250 A | 9/1978 | Davis | |
| 4,333,340 A | 6/1982 | Elmeskog | |
| 4,383,684 A | 5/1983 | Schliep | |
| 4,421,336 A | 12/1983 | Petrofsky et al. | |
| 4,480,830 A | 11/1984 | Petrofsky et al. | |
| 4,499,900 A | 2/1985 | Petrofsky et al. | |
| 4,509,509 A | 4/1985 | Bouvet et al. | |
| 4,520,827 A | 6/1985 | Wright et al. | |
| 4,558,704 A | 12/1985 | Petrofsky | |
| 4,580,569 A | 4/1986 | Petrofsky | |
| 4,586,495 A | 5/1986 | Petrofsky | |

(Continued)

FOREIGN PATENT DOCUMENTS

GB     2 392 110     2/2004

OTHER PUBLICATIONS

PCT Publication WO/03105744. Therapeutic Exercise System and Method for a Paralyzed and Nonparalyed Neuromusculoskeletal Training System. Published Dec. 24, 2003.*

(Continued)

*Primary Examiner* — Scott Getzow
*Assistant Examiner* — Amanda Patton
(74) *Attorney, Agent, or Firm* — King & Schickli, PLLC

(57) ABSTRACT

A device and methods for performing a closed-chain exercise for the lower extremities of a human subject and, in particular, the legs, using stimulation. The device may include a sled for receiving the subject and for translating to and fro between a first, lower position in which the legs are at least partially bent and a second, higher position in which the legs are less bent than in the first position. A stimulator is provided for facilitating the performance of the closed-chain leg exercise by the subject to move the sled between the first and second positions, either by way of electrical signals provided directly to the applicable muscles or by way of sensory (e.g., visual) stimulation, with or without electro-muscular stimulation. In another aspect, adaptive feed-forward control may also be used to enhance the exercise regimen performed using the device.

13 Claims, 21 Drawing Sheets

U.S. PATENT DOCUMENTS

| | | | |
|---|---|---|---|
| 4,586,510 | A | 5/1986 | Glaser et al. |
| 4,672,697 | A | 6/1987 | Schurch |
| 4,715,235 | A | 12/1987 | Fukui et al. |
| 4,724,842 | A | 2/1988 | Charters |
| 4,796,631 | A | 1/1989 | Grigoryev |
| 4,809,696 | A | 3/1989 | Laenger et al. |
| 4,834,073 | A | 5/1989 | Bledsoe et al. |
| 4,863,157 | A | 9/1989 | Mendel et al. |
| 4,867,143 | A | 9/1989 | Morin |
| 4,913,424 | A | 4/1990 | Pepin |
| 4,928,957 | A | 5/1990 | Lanier et al. |
| 4,947,836 | A | 8/1990 | Laenger et al. |
| 5,024,214 | A | 6/1991 | Hayes |
| 5,099,828 | A | 3/1992 | Duke |
| 5,116,296 | A | 5/1992 | Watkins et al. |
| 5,121,747 | A | 6/1992 | Andrews |
| 5,169,363 | A * | 12/1992 | Campanaro et al. ............ 482/96 |
| 5,263,913 | A * | 11/1993 | Boren ............................. 482/96 |
| 5,328,424 | A * | 7/1994 | Greco ............................. 482/73 |
| 5,330,516 | A | 7/1994 | Nathan |
| 5,540,735 | A | 7/1996 | Wingrove |
| 5,551,937 | A | 9/1996 | Kwo |
| 5,558,627 | A | 9/1996 | Singer et al. |
| 5,601,519 | A | 2/1997 | Comereski |
| 5,628,722 | A | 5/1997 | Solomonow et al. |
| 5,810,698 | A | 9/1998 | Hullett et al. |
| 5,810,747 | A | 9/1998 | Brudny et al. |
| 5,861,017 | A | 1/1999 | Smith et al. |
| 5,885,197 | A | 3/1999 | Barton |
| 5,938,571 | A | 8/1999 | Stevens |
| 5,940,911 | A | 8/1999 | Wang |
| 5,961,541 | A | 10/1999 | Ferrati |
| 5,967,956 | A | 10/1999 | Teeter |
| 6,064,911 | A | 5/2000 | Wingrove |
| 6,064,912 | A | 5/2000 | Kenney |
| 6,152,855 | A | 11/2000 | Dean, Jr. et al. |
| 6,243,897 | B1 | 6/2001 | Sumiya |
| 6,282,448 | B1 | 8/2001 | Katz et al. |
| 6,393,328 | B1 | 5/2002 | McGraw et al. |
| 6,456,884 | B1 | 9/2002 | Kenney |
| 6,456,885 | B1 | 9/2002 | Shiba et al. |
| 6,464,296 | B1 | 10/2002 | Sumner |
| 6,564,103 | B2 | 5/2003 | Fischer et al. |
| 6,678,563 | B2 | 1/2004 | Fang et al. |
| 6,690,155 | B2 | 2/2004 | Vig et al. |
| 6,701,189 | B2 | 3/2004 | Fang et al. |
| 6,725,094 | B2 | 4/2004 | Saberski |
| 6,728,577 | B2 | 4/2004 | Minogue et al. |
| 6,788,976 | B2 | 9/2004 | Gesotti |
| 6,876,883 | B2 | 4/2005 | Hurtado |
| 7,011,605 | B2 * | 3/2006 | Shields ............................. 482/8 |
| 7,056,297 | B2 | 6/2006 | Dohno et al. |
| 7,181,793 | B2 | 2/2007 | Lee |
| 7,381,192 | B2 * | 6/2008 | Brodard et al. ................... 601/5 |
| 2003/0208246 | A1 | 11/2003 | Kotlik et al. |
| 2004/0023759 | A1 | 2/2004 | Duncan et al. |
| 2004/0044381 | A1 | 3/2004 | Duncan et al. |
| 2004/0082979 | A1 | 4/2004 | Tong et al. |
| 2004/0127954 | A1 | 7/2004 | McDonald, III |
| 2004/0147975 | A1 | 7/2004 | Popovic et al. |
| 2004/0172093 | A1 | 9/2004 | Rummerfield |
| 2004/0172097 | A1 | 9/2004 | Brodard et al. |
| 2004/0236384 | A1 | 11/2004 | Dar et al. |
| 2005/0015118 | A1 | 1/2005 | Davis et al. |
| 2005/0107831 | A1 | 5/2005 | Hill et al. |
| 2005/0278001 | A1 | 12/2005 | Qin et al. |
| 2005/0283204 | A1 | 12/2005 | Buhlmann et al. |
| 2006/0247095 | A1 | 11/2006 | Rummerfield |
| 2006/0293156 | A1 * | 12/2006 | Trees ............................. 482/148 |

OTHER PUBLICATIONS

Trees, Darin. Therapeutic Exercise Device. PCT Publication WO 2004/039301. Published May 13, 2004.*

Wassermann, Schneeberger; A Highly Flexible Online Controllable FES-Pattern Generator for Basic Research, Vienna University of Technology, Institute for Machine Dynamics and Measurement; Austria, Printed Jun. 27, 2006.

Riess, Abbas; Adaptive Neural Network Control of Cyclic Movements Using Functional Neuromuscular Stimulation; IEEE Trans Rehabil Eng; Mar. 2000, 42-52; vol. 8; Center for Biomedical Engineering, University of Kentucky; Lexington, KY.

Abbas, Triolo; Experimental Evaluation of an Adaptive Feedforward Controller for Use in Functional Neuromuscular Stimulation Systems; IEEE Trans Rehabil Eng; Mar. 1997, 12-22 vol. 5; Center for Biomedical Engineering, Wenner Gren Research Laboratory, University of Kentucky; Lexington, KY.

Abbas, Chizeck; Neural Network Control of Functional Neuromuscular Stimulation Systems: Computer Simulation Studies; IEEE Trans Biomed Eng; Nov. 1995; 1117-27, vol. 42, Biomedical Engineering Program, Catholic University of America; Washington D.C.

Riess, Abbas; Adaptive Control of Cyclic Movements as Muscles Fatigue Using Functional Neuromuscular Stimulation; IEEE Trans Neural Syst Rehabil Eng; Sep. 2001; 326-330, vol. 9; Center for Biomedical Engineering, University of Kentucky; Lexington, KY.

Stites, Abbas; Sensitivity and Versatility of an Adaptive System of Controlling Cyclic Movements Using Functional Neuromuscular Stimulation; IEEE Trans Biomed Eng; Sep. 2000; 1287-92, vol. 47; Department of Mathematics, University of Kentucky; Lexington, KY.

Hartman; Abstract; Adaptive Stimulator for Exercise and Rehabilitation; CRISP, Feb. 25, 2002, 2 pps., Versailles, KY.

Hartman; Abstract; Kinematic Biofeedback for Independent Motor Retraining; CRISP, May 1, 2005, 2 pps., Versailles, KY.

Hartman; Abstract; Stimulation-Augmented Exercise and Neuromotor Therapy; CRISP, May 1, 2006, 2 pps., Versailles, KY.

* cited by examiner

| NAME | VALUE | UNIT |
|---|---|---|
| F_diff_max | 1000 | Newton |
| k_GRF_diff | 0.5 | Newton |
| GRF_Threshold | 2 | Newton |
| Boot Range | 60 | Degree |
| Theta k_Max | 60 | Degree |
| Vel_k_Max | 37.6929 | Degree/Second |
| Pos_Learning Rate | 1 | |
| GRF_LR | 0.1 | |
| Vel_LR | 0.05 | |
| Max Timesteps | 120 | |
| Num Neurons | 240 | |
| Posn Filter Order | 30 | |
| Vel Filter Order | 60 | |
| Neuron Offset | 0.05 | |
| Neuron Width | 0.45 | |
| Num Active | 9 | |

*Fig. 7a*

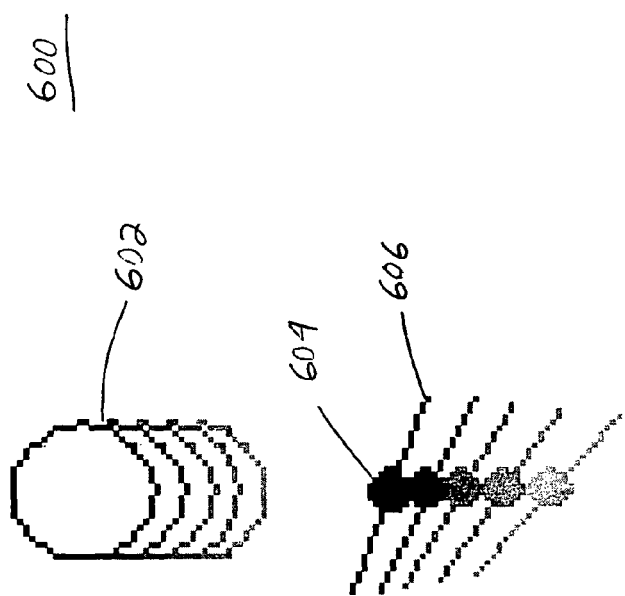

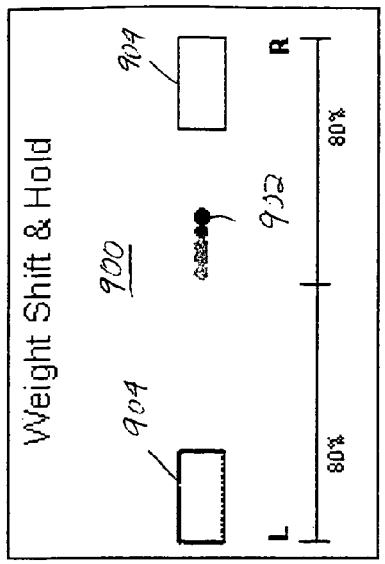
Fig. 13a  Fig. 13b  Fig. 13c
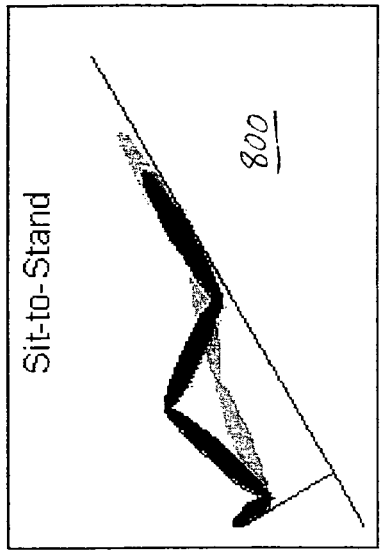
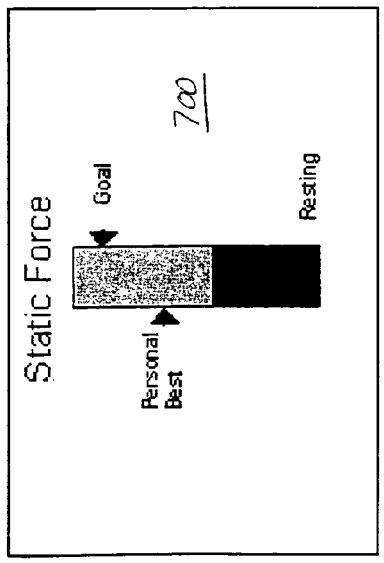
Fig. 13d
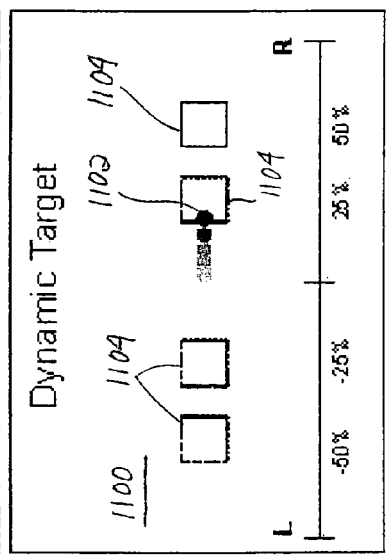
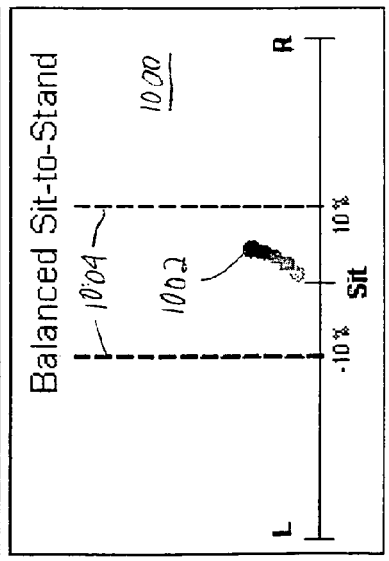
Fig. 13e

LOWER EXTREMITY EXERCISE DEVICE WITH STIMULATION AND RELATED METHODS

This application claims the benefit of U.S. Provisional Patent Application Ser. No. 60/697,772, filed Jul. 8, 2005, the disclosure of which is incorporated herein by reference.

GOVERNMENT RIGHTS

Certain aspects of the disclosed inventions were made with support under grants from the National Institutes of Health, National Institute of Child Health and Development, and the National Center for Medical Rehabilitation Research (Grant Nos. NIH-NICHD NCMRR 1-R43-HD39013, NIH-NICHD NCMRR 1-R44-HD39013, and NIH-NINDS 1-R43-NSO45448). The government may have certain rights in this invention.

COPYRIGHT STATEMENT

A portion of the disclosure of this document contains material subject to copyright protection. No objection is made to the facsimile reproduction of the patent document or this disclosure as it appears in the Patent and Trademark Office files or records, but any and all rights in the copyright(s) are otherwise reserved.

TECHNICAL FIELD

The present inventions relate to the human exercise and rehabilitation arts and, more particularly, to devices for facilitating the performance of a closed-chain lower extremity exercise with stimulation and related methods.

BACKGROUND OF THE INVENTION

Facilitating exercise using external stimulation, including by sending electrical pulses to contract or otherwise activate the targeted or involved muscles, is known in the art. Typically, the electrical pulses applied are generated by an external stimulator, and travel through associated wires to electrode pairs placed on the skin adjacent the muscle(s) to be contracted. The electricity passing through the skin causes the targeted muscle fibers to activate or contract, even without voluntary control by the subject. Accordingly, such stimulation is frequently used in situations where the subject is incapacitated or otherwise unable to control function of the muscles, such as where an injury to the brain or associated portion of the nervous system has occurred.

Despite the widespread past use of electrical stimulation for exercising muscles, certain limitations in the application of this technology and the results produced remain. For instance, while electrically stimulating resting leg muscles alone provides a moderate benefit, a significantly better degree of exercise may be achieved when the legs are also subjected to movement through a particular range of motion (ROM). Although such movements could be manually done by a physical therapist or like assistant concurrently with the application of electrical stimulation, the benefit would be greater if the leg muscles being stimulated, as well as others that are not, undergo active or dynamic loading (and especially the type of loading that would occur as the result of normal exercise or ambulation). Such dynamic loading is thought to help the otherwise paralyzed or inactive muscles build mass, strength, and endurance at levels that cannot be achieved through stimulation alone, and also reduces the rate of loss in bone mineral density.

Many incapacitated subjects, and in particular those who have experienced spinal cord injury resulting in the partial or total loss of use of the lower extremities, often find exercise via mere electrical stimulation through contact electrodes tedious. The stimulation of otherwise non-operational or paralyzed muscles typically occurs while the subject simply lies prostrate or sits because of the inability to stand or ambulate independently. Besides again avoiding the desirable dynamic loading, the bored subject undergoing treatment while laying still on a table also does not gain the mental and emotional benefits resulting from the exercise and the concomitant sense of accomplishment. Consequently, "exercising" via stimulation alone can be viewed negatively by those most in need of the resultant benefits, and does not provide the desired level of encouragement to promote the most expeditious recovery, where possible.

Even if current stimulation techniques are applied to closed-chain leg exercises under partial bodyweight loading, the inability to account for differences in the ground reactive force, or GRF, experienced by each leg creates potential problems. If the muscles of one leg are doing more of the work than those of the other, and this disparity not kept in check, less-than-optimal results may be achieved. This is particularly true when the loss of leg muscle function is asymmetrical.

Accordingly, a need is identified for a manner in which to combine the benefits achieved through electrical muscle stimulation with those of load bearing, closed-chain exercise, including for subjects with a full or limited inability to use the muscles their lower extremities (and, in particular, one or both of their legs). This may even include situations where a full loss of muscle control has occurred, such as in the case of paraplegia, or control is lost to different degrees in each leg, such as in the case of stroke.

SUMMARY OF THE INVENTION

In accordance with one aspect of the invention, a device for performing a closed-chain exercise for the lower extremities of a human subject and, in particular, the legs, using stimulation is disclosed. The device comprises a frame and a sled for receiving the subject facing generally upwardly. The sled is mounted to the frame for translating to and fro between a first, lower position in which the legs are at least partially bent and a second, higher position in which the legs are less bent than in the first position. An associated stimulator facilitates the performance of the closed-chain leg exercise by the subject so as to move the sled between the first and second positions.

Preferably, the sled is slidably mounted to the frame, and the device further includes a base for supporting the frame above the ground. Still more preferably, the stimulator is an electrical stimulator for supplying electrical pulses to muscles of the subject, such as by way of electrodes placed on the adjacent surface of the subject's skin to effect autonomous performance of the exercise. Alternatively, the stimulator may comprise a visual stimulator for displaying information for encouraging the subject to move the sled voluntarily from the first position to the second position.

In one embodiment, an angle of the frame relative to a horizontal plane is adjustable. The device may also include in this or another embodiment a pedal support for supporting at least one of the user's feet. The pedal support further includes a sensor for determining a ground reactive force exerted during the exercise. Preferably, the pedal support comprises a receiver mounted for pivoting as the sled moves from the first position to the second position, and further including means for determining a relative position of the receiver. The device may further include means for adjusting the stimulation based on a sensed ground reactive force, as well as means for assisting in unbending the legs in the second position.

In accordance with another aspect of the invention, a method of performing a closed-chain leg extension exercise on a human subject with full or partial loss of muscular control is disclosed. The method comprises positioning the subject on a sled movable between a first, lower position with the legs at least partially bent to a second, higher position in which the legs are less bent than in the first position. The method further comprises stimulating the subject to move the sled from the first position toward the second position and thus perform the leg extension exercise.

Preferably, the stimulating step comprises applying electrical pulses to the subject's leg muscles to move the sled autonomously from the first position toward the second position. The stimulating step may further comprise visually displaying on a display information for encouraging the subject to move the sled voluntarily from the first position toward the second position. This information may comprise an indication of the level of ground reactive force exerted by each leg during the exercise.

In accordance with still another aspect of the invention, a method of performing a closed-chain leg extension exercise on a human subject with full or partial loss of leg muscle control is disclosed. The method comprises electrically stimulating at least a portion of the leg muscles at a predetermined level to move the legs between a first, bent position and a second, extended position during the closed-chain leg extension exercise. Upon sensing a parameter of the exercise, the predetermined level of electrical stimulation may be adjusted to a revised level based on the sensed parameter. At least a portion of the leg muscles are then stimulated at the revised level.

In one embodiment, the subject's feet are associated with a pedal receiver during the exercise, and the sensing step comprises measuring an angle associated with the pedal receiver as the sensed parameter. The method further includes the step of comparing the measured angle with a predetermined angle to determine a variation, while the adjusting step comprises determining the revised level based on the variation.

In this or another embodiment, the subject is positioned on a sled. The sensing step may comprise detecting a velocity error signal. In such case, the adjusting step comprises determining the revised level of stimulation based on the velocity.

In this or still another embodiment, the sensing step comprises measuring ground reactive forces produced by the legs during the exercise. In such case, the method further includes the step of balancing the ground reactive forces, and the adjusting step comprises determining the revised level of stimulation based on the balanced ground reactive forces. The method may still further include the step of adjusting the levels of electrical stimulation provided to the left and right legs based on the sensed ground reactive forces.

In accordance with yet another aspect of the invention, a device for performing a closed-chain leg extension exercise on a human subject with full or partial loss of leg muscle control is disclosed. The device comprises means for electrically stimulating at least a portion of the leg muscles at a predetermined level so as to move the legs between a first, bent position and a second, extended position during the closed-chain leg extension exercise. Means for sensing a parameter of the exercise is also provided, along with means for electrically stimulating the portion of the leg muscles at a revised level based on the sensed parameter.

In one embodiment, the means for electrically stimulating at the revised level includes means for adjusting the predetermined level of stimulation based on the sensed parameter. Likewise, the sensing means comprises a sensor for measuring a parameter selected from the group consisting of ground reactive force, velocity, and pedal angle.

In accordance with a further aspect of the invention, a device for performing an exercise for the lower extremities of a human subject and, in particular, the legs, using stimulation and with the feet in contact with a stable support structure is disclosed. The device comprises means for facilitating movement of the subject to and fro between a first position in which the legs are at least partially bent and a second position in which the legs are at least partially extended while the feet remain in contact with the stable support structure. Means for measuring the ground reactive force exerted during the exercise also forms part of the device.

In one embodiment, the device further includes an electrical stimulator for supplying electrical pulses to muscles of the subject via electrodes placed on the adjacent surface of the subject's skin. In another embodiment, the stimulator provides information for encouraging the subject to move the sled from the first position to the second position, such as an indication regarding the measured ground reactive force. The device may further include means for assisting in unbending the legs in the second position.

BRIEF DESCRIPTION OF THE DRAWINGS

FIG. 2b is a partial, slightly enlarged perspective view of the exercise device of FIG. 2a;

FIG. 3a is a perspective view of the sled used in the exercise device of FIG. 2a;

FIG. 4 is a front view of a single boot used in the exercise device of FIG. 2a;

FIGS. 12 and 13a-13e show various screen shots that may be used in connection with visually stimulating exercise.

DETAILED DESCRIPTION OF THE INVENTION

Figure 1:
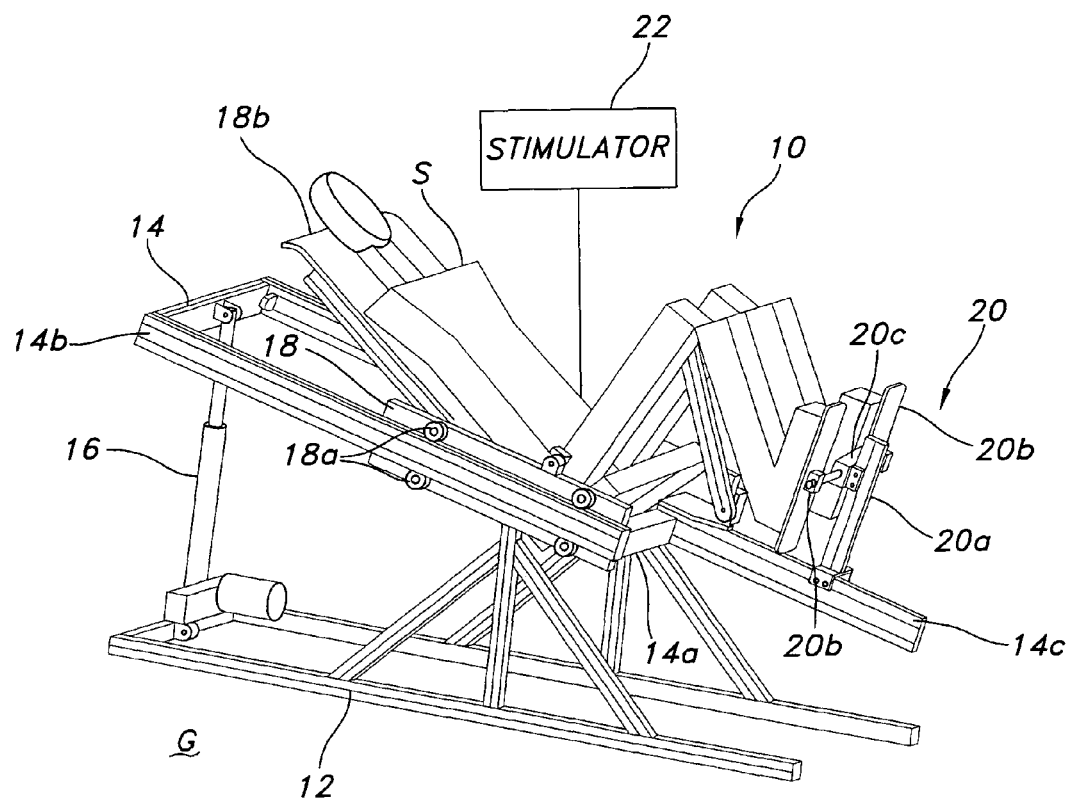
FIG. 1 is a schematic view of one embodiment of an exercise device arranged in accordance with the principles of the present invention.

Reference is now made to FIG. 1, which schematically depicts an exercise device 10 forming one aspect of the present invention. In the illustrated embodiment, the device 10 facilitates performing closed-chain leg extension exercises (sometimes referred to in the vernacular as "knee bends" or "squats") done by the legs autonomously (i.e., without the use of the arms) against the direction of gravity. More specifically, the illustrated device comprises a base 12 supporting an associated guide frame 14 in an elevated fashion. Together, these components of the device 10 support the body weight of an exercise subject S above the ground G and facing generally upwardly in a stable, secure fashion.

Preferably, the frame 14 is mounted to the base 12 in a manner that permits it to be angularly adjusted with respect to a horizontal plane, or one generally parallel to level ground G. For instance, as shown in FIG. 1, a first end 14a of the frame 14 is mounted to the base 12 for pivotal movement relative to the horizontal plane through a range of angles, while the opposite end 14b is connected to a height-adjustable support 16. In perhaps the simplest form, this support 16 may take the form of a pair of telescoping tubular members, one of which can be locked into position relative to the other to hold the corresponding end 14b of the frame 14 at the desired height. However, a motorized jackscrew, ball screw, linear actuator or like motorized adjustment device could also be used for tilting the frame 14 to achieve a desired angle relative to the horizontal plane (which a skilled artisan will appreciate necessarily adjusts the amount of loading on the legs during a leg extension exercise).

Besides connecting to the base 12, the frame 14 is also adapted for receiving a sled 18 or other means for facilitating performance of the closed-chain leg extension exercise in a manner such that it may translate to and fro in a longitudinal direction between a first, lower position and a second position higher in elevation than the first position. These positions generally correspond to a bent position of the subject's legs and one in which the legs are less bent, and preferably mostly or fully extended or erect. In the embodiment of FIG. 1, this is done by providing the sled 18 with outwardly projecting bearings in the form of spaced pairs of rotatably mounted guide rollers 18a. These rollers 18a may engage opposite sides of the longitudinal members of the frame 14 and thus not only capture it in place, but also allow it to translate from the first end 14a to the second end 14b with reduced friction. Instead of such an arrangement, and as will be further appreciated upon reviewing the following description, it is possible to mount the translating sled 18 to the frame 14 in a myriad of ways, including using static block bearing(s) captured in associated guide tracks.

The sled 18 in turn includes an inclined seat 18b creating a surface for receiving and supporting the exercise subject in a generally seated condition. More particularly, this seat 18b is generally L-shaped, with a first portion for supporting the upper torso of the exercise subject and a lower, generally transverse second portion providing a resting surface for the buttocks and upper backside of the subject's legs. This second portion of the seat 18b is preferably truncated in the vertical direction such that legs of the subject, when seated, project beyond the end of both the sled 18 and the associated portion of the guide frame 14. The planes of the first and second portions 18b of the seat are preferably at an obtuse angle (note angle a in FIG. 3a) in order to ensure proper positioning of the subject's feet relative to the receiver 20 and overall comfort throughout the cycle.

The device 10 also includes a pedal support in the form of a receiver 20 for receiving and providing an engagement surface one or both of the subject's feet. In the illustrated embodiment, this receiver 20 is constructed as an extension 14c from the first end 14a of the frame 14 and includes a generally upstanding member 20a. This upstanding member 20a in turn supports transversely extending, spaced pedal supports in the form of footplate assemblies 20b including a transverse post and a plate for engaging the subject's feet in a planar fashion (which may also include appropriate straps or holders; not shown). Although preferably held securely in place by fasteners or otherwise fixed, the support base 20c for the footplate assemblies 20b may alternatively be adjustable along the extent of the upstanding member 20a, and the upstanding member 20a in turn fastened to, but independently adjustable along, the extension 14c of the frame 14 (which may include regular linear gradations to facilitate positional repeatability). As a result, adjustments can be easily and reliably made to accommodate the specific subject or to facilitate a desired pattern or range of movement during the leg extension exercise.

In a basic mode of operation, the sled 18 initially locates at a home or resting position adjacent the first end 14a of the frame 14 (but not necessarily at the terminal end of the range of movement). A subject having full or partial loss of use of their leg muscles or otherwise in need of stimulation-assisted exercise is positioned on the seat 18b with their feet engaging the corresponding pedal receivers 20 in the manner shown in FIG. 1 (thus forming the closed-chain mode of exercise). Before or during placement of the subject on the device 10, the sled 18 may also be moved to a terminal position at the first end 14a and locked in place by a pin or the like, if necessary or desired for a particular application or simply for purposes of comfort (and a "lockout" sensor (not shown) may be provided for preventing the application of electrical stimulation while the sled is in the locked condition). Chest straps, shoulder pads or rests, and/or a head rest (not shown, but see FIG. 2) are preferably provided for holding the subject securely in place in the desired position on the sled 18 during the exercise. Adjustments to the upstanding member 20a may also be made along extension 14c to vary the range of motion (i.e., the depth of the squat).

If not previously done, the angular relationship of the frame 14 relative to the horizontal may be adjusted as desired to provide a certain amount of dynamic loading on the legs during the exercise at the result of the subject's own body weight (with a lower angle of course producing concomitantly less loading than a higher one). Typically, the frame 14 will be maintained initially at a low, but positive acute angle relative to the horizontal to enable the subject to be placed more easily on the seat 18b in a comfortable position with minimal, if any, body weight load on the legs, and then increased accordingly. In any case, once in the desired position on the device 10 and any locking device arranged such that the sled 18 may freely move to and fro along the frame 14.

At that point, at least the subject's upper leg extensor muscles, and typically also certain lower back muscles, are electrically stimulated through one or more pairs of strategically placed electrodes using an external stimulator 22 of a type generally known in the art (such as, for example, the OCTOSTIM electrical muscle stimulator distributed by Freiler of Santa Cruz, Calif., which can simultaneously activate eight electrode pairs). This stimulation contracts the necessary muscles as required to cause or otherwise forcibly assist the legs in extending through a range of motion from the bent to an extended condition and with at least partial body weight loading. Specifically, the legs move from a generally relaxed or passive, bent resting position (typically when the sled 18 is at its lower terminus of the first end 14a of the frame 14) toward an active position in which the legs are less bent and with the subject's body weight at least partially supported or carried by the stimulated muscles (typically with the sled 18 away from the first end 14a of the frame and higher than when in the initial position, but not necessarily at the second end 14b). Although the particular muscles stimulated, the location of the electrodes, the level of stimulation, and the pulse parameters necessary to cause the subject to involuntarily extend their legs in such a manner may vary depending on the particular application or situation (and is believed to be fully within the purview of one of ordinary skill in the art), an exemplary approach generally involves placement of electrodes as necessary to stimulate the left and right quadriceps and hamstrings, the gluteus maximus, and the erector spinae muscles of the lower back.

During this dynamic loading cycle, the sled 18 of course translates longitudinally along the inclined frame 14 from the first, lower end 14a toward the second, higher end 14b, while the subject remains comfortably seated in a stable fashion with their feet securely held by the receiver 20 and their arms at rest. As a result, a full range of motion of the legs and associated muscles may be automatically achieved, with independent loading created as a result of the at least partial body weight acting on the leg muscles, bones, and joints, regardless of whether the subject is able to perform the exercise voluntarily. A better degree of exercise is thus afforded than would otherwise be achieved using electrical stimulation alone, and in a safe, reliable, and highly regular/repeatable closed-chain fashion with a minimum amount of shear at the knee or other joints being exercised.

Moreover, the ability of the subject to remain comfortably seated (including with a view of the legs performing the exercise as a result of the inclined nature of the seat 18b), as well as the sense of accomplishment from moving the sled 18 along the frame 14, provides an overall better sensory experience as compared to stimulation alone. This creates a concomitant desire to repeat the exercise successfully. Successful completion of the exercise also facilitates motor retraining due to tactile and somatosensory feedback to the spinal cord and/or brain. Additionally, the inclined nature of the seat 18b advantageously provides a non-weight-bearing resting position and minimizes slippage of the subject downward with repeated exercise cycles, thus ensuring comfort throughout.

Once the legs are extended with the sled 18 higher than in the initial position and at least somewhat closer to the second end 14b of the frame 14, the stimulation provided through the electrodes may cease, either automatically or as the result of a signal from an associated controller (not shown in FIG. 1), which may include a remote input device (not shown) manually operated by an assistant. In situations where the subject has sufficient control of the corresponding muscles, he or she may cause the leg extension exercise to cease post-stimulation by relaxing the now-active muscles or bending at the knees, if locked during the exercise, at which point the legs may return to a non-extended position. With the muscles relaxed and/or the knees unlocked, the sled 18 reverts toward the opposite end of the frame 14 and the legs return to the bent position, as shown in FIG. 1.

To facilitate this return and ensure that it is achieved in a stable, reliable fashion, dampers, springs, or like damping means (not shown) may be provided along the frame 14 for slowing the movement of the sled 18 during the return to the home position. Similar dampers or the like may also be provided adjacent the first and second ends 14a,14b of the frame 14 to smooth the movement at the terminal ends of the exercise cycle and avoid potentially deleterious collisions between the seat 18b and the frame 14.

In situations where the subject has complete loss of muscle control in their lower extremities or otherwise unable to unlock their knees voluntarily and return their legs to the bent position shown in FIG. 1, the end of the stimulation may also leave both legs fixed in the extended position (and electrical stimulation of the involved muscles cannot unbend the knees). In such case, the return of the sled 18 to a rest position (e.g., at the first end 14a of the frame 14) would thus not be automatically achieved. Although "unlocking" of the extended legs may be manually accomplished by an assistant, another aspect of the invention not shown in FIG. 1, but detailed further in the description that follows, is a knee flexion actuator that helps to return the subject's legs to an unbent, or resting condition and assume the first position. The exercise may then be repeated as desired or necessary to follow a pre-planned regimen.

Despite the viability of this basic technique for effecting exercise of the lower extremities with electrical stimulation and independent loading of the associated muscles being advantageously afforded, it also may be desirable to combine it with a measure of automatic and adaptive feed-forward control to still further improve the quality of the resulting exercise (and without the need for active manual control provided by an assistant). For example, by sensing the GRF exerted by each leg through the pedal receiver 20 during the exercise, the amount of electrical stimulation afforded may be precisely adapted to ensure that a better exercise result is achieved and that both legs are working together in a generally equal fashion to perform the exercise. Stated perhaps more simply, it is preferable to have both legs experience the same amount of exercise through partial bodyweight loading, and to provide realtime control of the amount of stimulation through feedback to achieve this result. Likewise, by automatically adjusting the stimulation to address and compensate for the inevitable effects of fatigue, a more complete or thorough exercise session may result, and one especially adapted for the abilities of the particular subject.

Figure 2A:
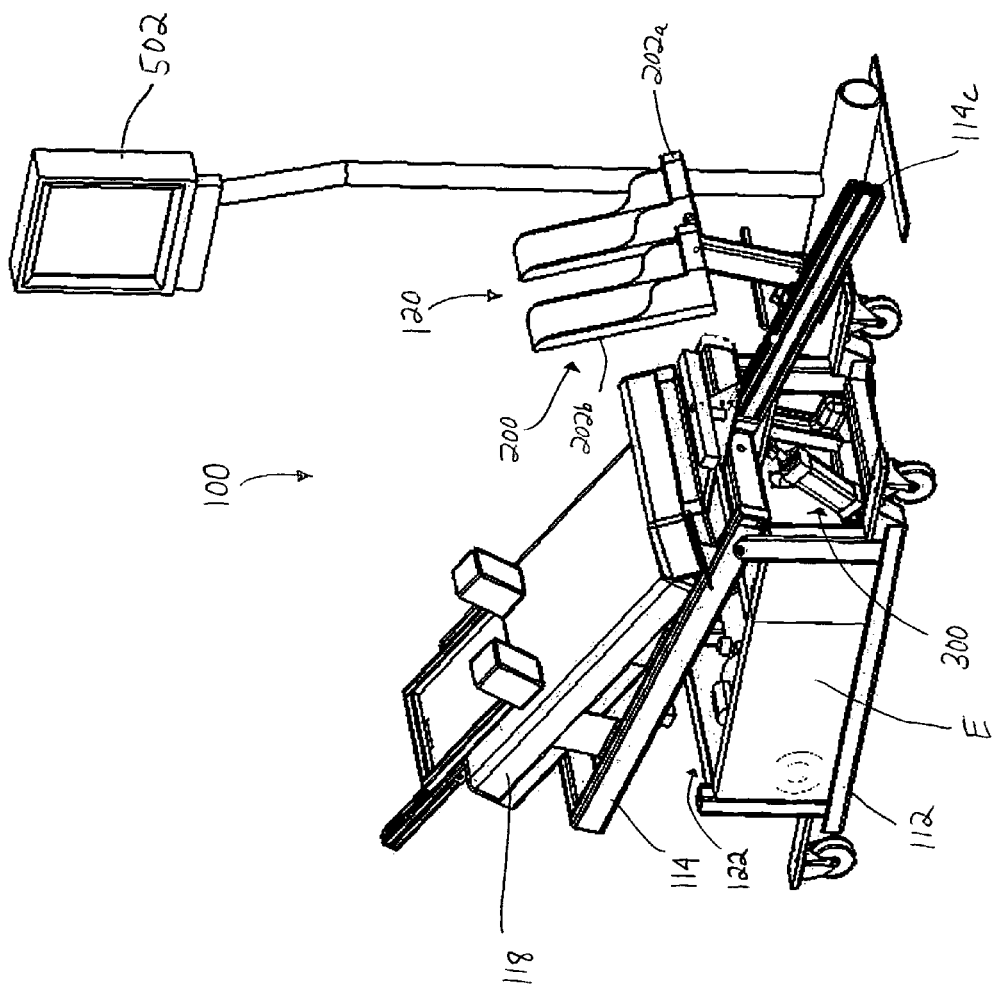
FIG. 2a is a perspective view of another embodiment of an exercise system arranged in accordance with the principles of the present invention.
Figure 2B:
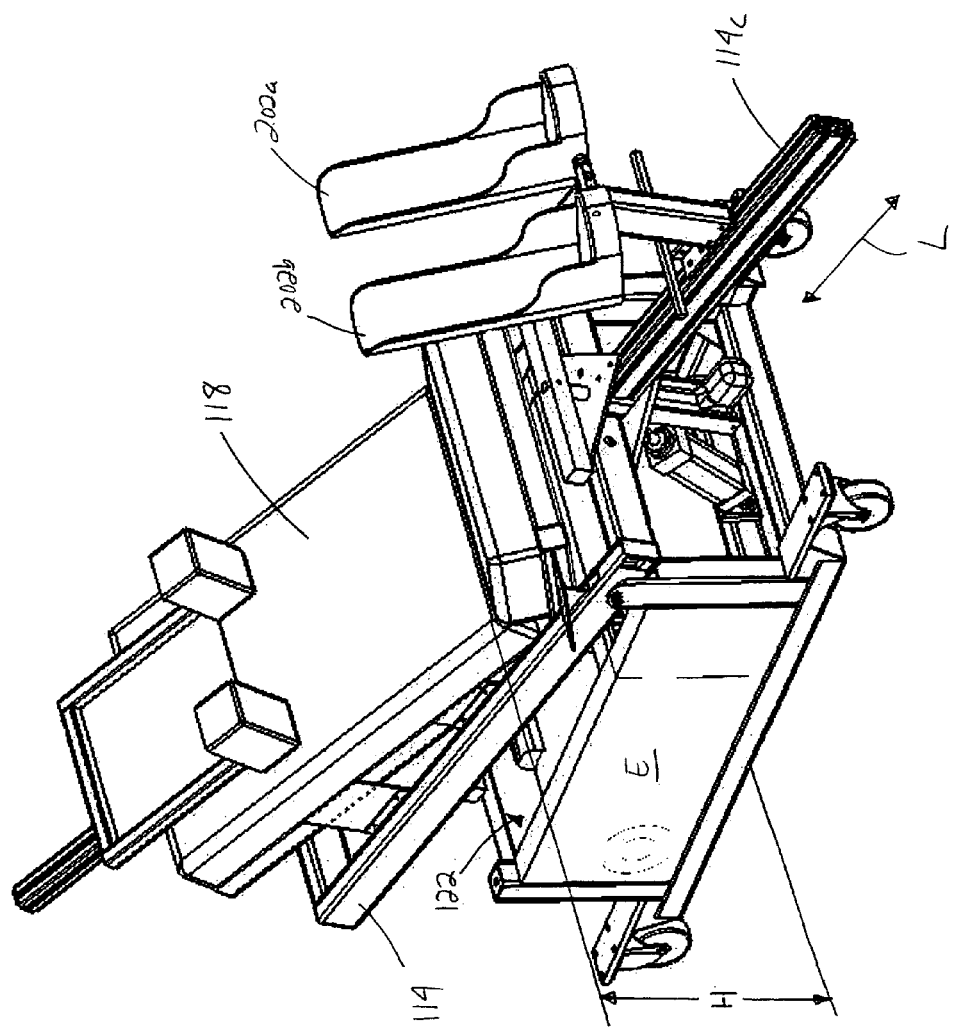
Figure 3A:
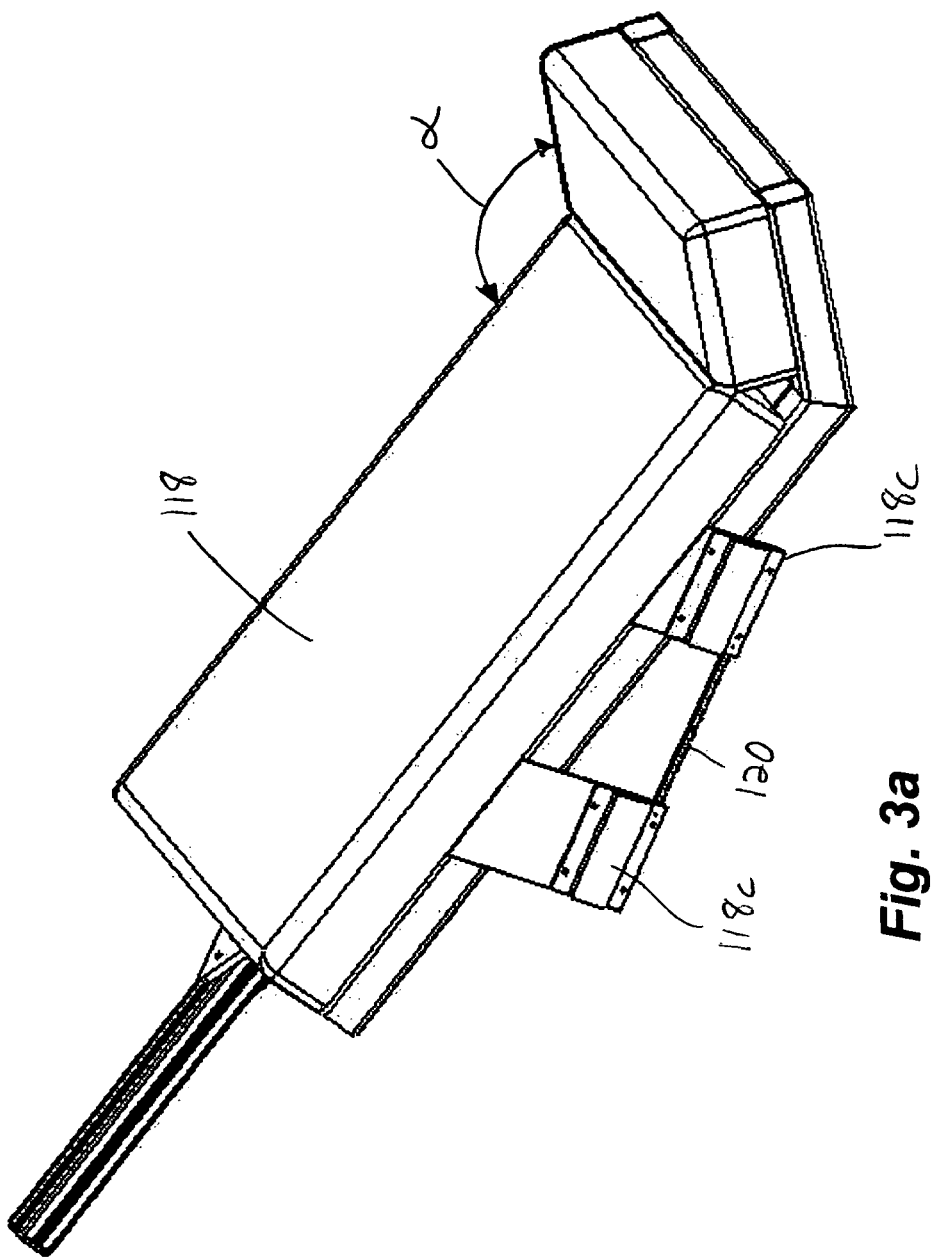
Figure 3B:
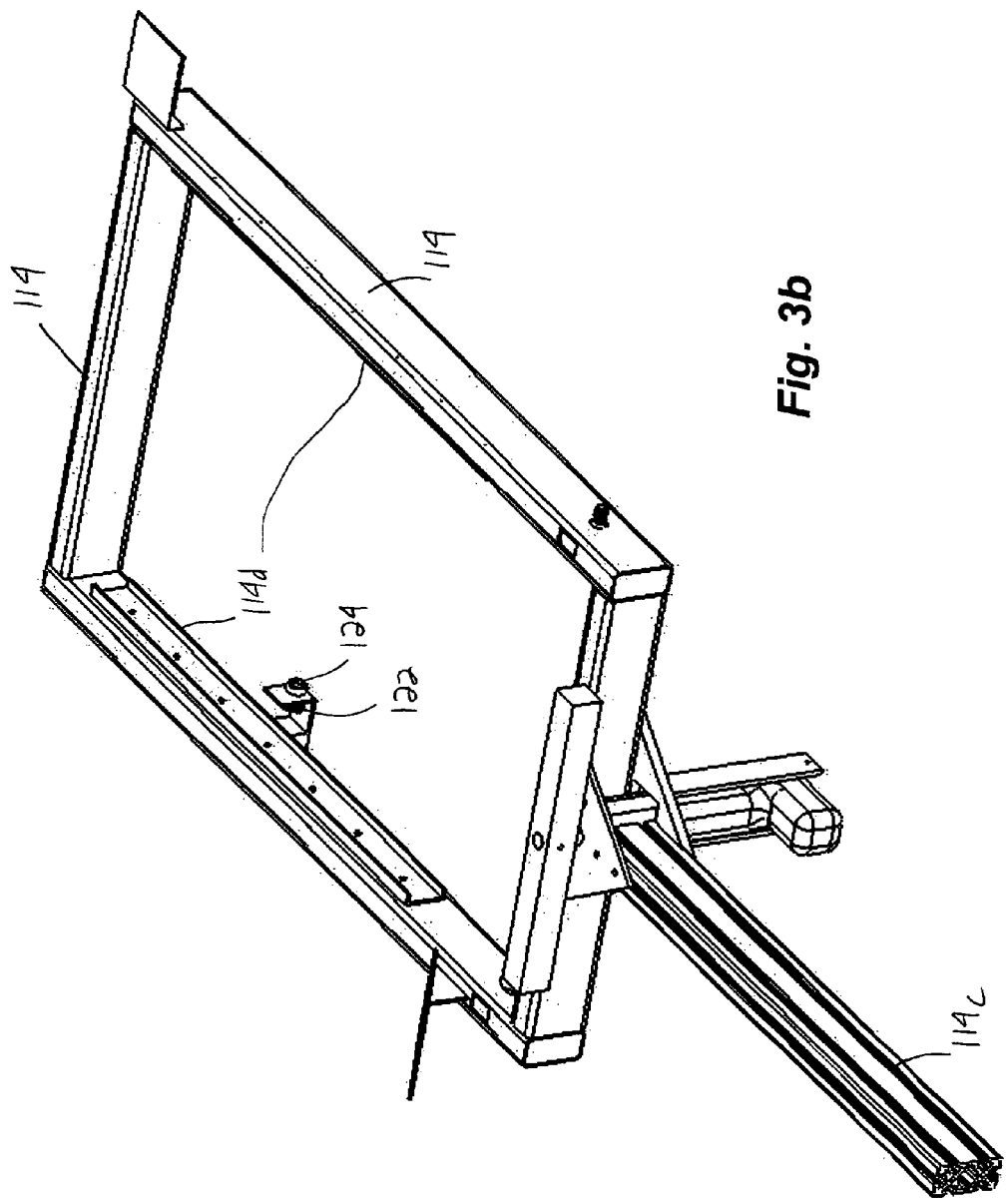
FIG. 3b is a perspective view of a frame for supporting the sled.

To facilitate this result, and with reference now to FIGS. 2a and 2b, another embodiment of the exercise device 100 is depicted and described. This device 100 is designed especially to accommodate the application and use of adaptive feedback control, versions of which are generally known in the art. First describing the mechanics, this embodiment of the device 100 includes a base 112, an angularly adjustable frame 114, a sled 118, and an associated stimulator 122, similar to the first embodiment of the device 10 outlined in the foregoing description. However, instead of mounting the sled 118 to the frame 114 using rollers, static bearing blocks 118c are shown in FIGS. 3a and 3b as providing the low friction support. These bearing blocks 118c are in turn slidably received in and captured by elongated guide tracks 114d formed in the opposed sides of the frame 114 (FIG. 3b). Consequently, the sled 118 remains fully capable of moving to and fro in a longitudinal direction along the frame 114 between first, lower and second, higher ends 114a, 114b with reduced friction.

Figure 4:
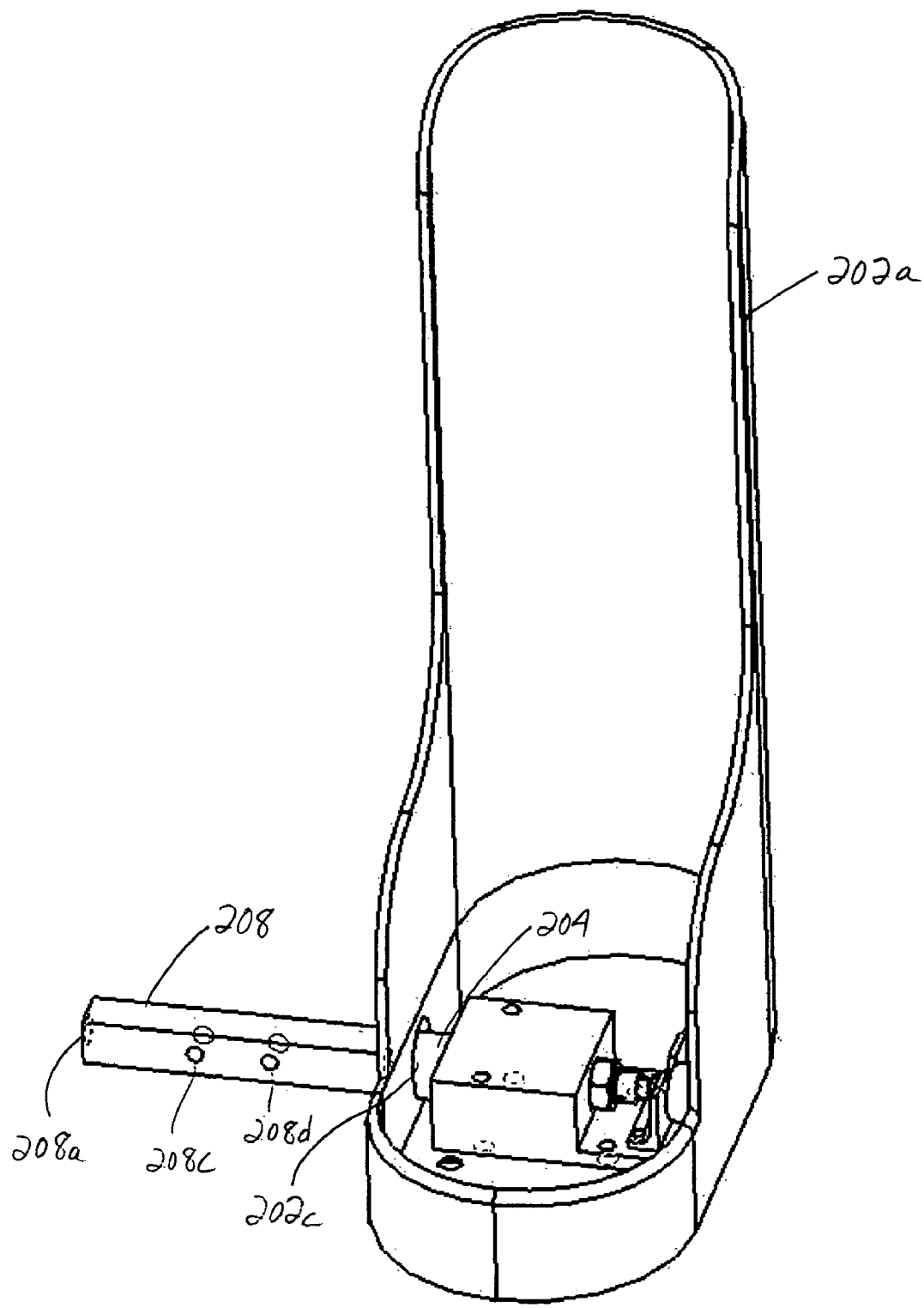

Also in this embodiment, the pedal support or receiver 120 takes the form of a boot assembly 200 including a pair of spaced boots 202a, 202b for receiving at least the left and right feet of the exercise subject, respectively, when seated on the sled 118. As perhaps best shown in FIGS. 4 and 5, these boots 202a, 202b are generally elongated for receiving and supporting not only the respective feet, but also the lower portion of the subject's legs from a point just below the knee. In connection with straps or like adjustable attachment means, these elongated boots 202a, 202b help to ensure that the subject's knees and hips are held laterally stable during the exercise such that the force from the stimulated muscle is translated through the legs to the pedal receiver 120 or footplate assembly. Each boot 202a, 202b also includes a receiver 202c or opening for receiving a transverse support post 204 (FIG. 4) to which it is mounted for pivoting movement through at least a range of angles necessary to accommodate the subject's legs during the full range of motion that might occur during the exercise (typically less than 90°, and usually closer to 60°).

Figure 5:
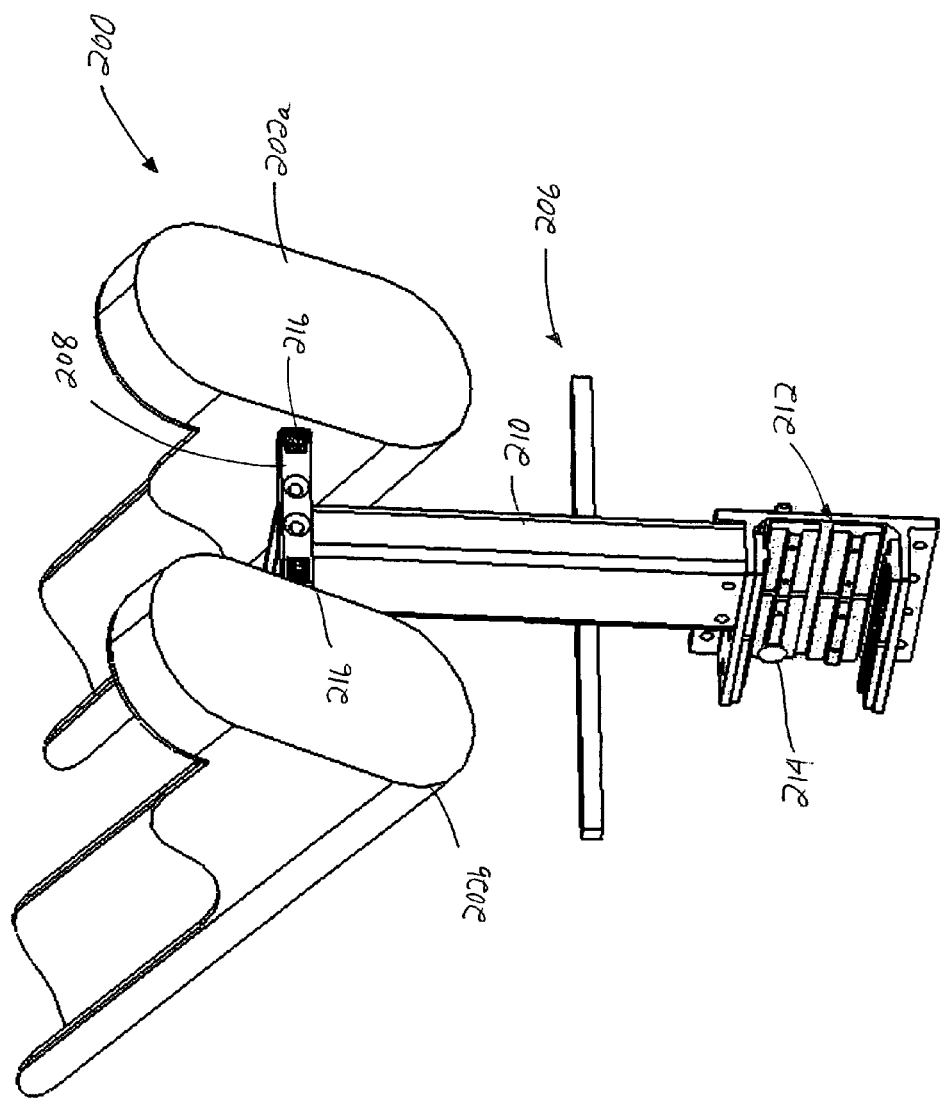
FIG. 5 is a perspective depiction of a boot assembly.

Turning now also to FIG. 5, the boots 202a, 202b preferably mount with the ability to facilitate adjustments and accommodate a particular user or desired range of motion.

Accordingly, as illustrated, the transverse support posts 204 may be associated with a support assembly 206 including a transverse support bar 208. This bar 208 in turn includes opposed apertures (only one aperture 208a shown in FIG. 4) for receiving the end of each post 204 associated with each boot 202a, 202b. The bar 208 also includes apertures 208c, 208d for receiving fasteners associated with a mount 210 (and may also be height adjustable therealong by using a bracket (not shown) to form the connection). The mount 210 includes a channel 212 for slidably receiving the frame extension 114c.

As a result of this arrangement, adjustability in a generally longitudinal direction L can be made by moving the entire assembly 206 along the frame extension 114c through the channel 212 slidably receiving it. This of course offers a measure of height adjustability for the subject's feet, and also leads to an adjustment in the boot angle and the concomitant range of motion. Since this direction L is also generally aligned with the direction of travel of the sled 118 during the exercise, a locking device is preferably provided, such as a spring-biased pin 214 for associated with a plurality of spaced apertures formed in the extension 114c. However, a similar detent, thumb screw, or like arrangement could also be used instead.

To provide feedback control using known adaptive algorithms as a means for facilitating or ensuring proper performance of the leg extension exercise, it is generally desirable to have an approximate measure of the GRF exerted by each of the subject's legs during the exercise so that a comparison and appropriate correction can be made. To facilitate such estimation, the boots 202a, 202b may be "instrumented" to measure the approximate GRF for each leg during the exercise. In one embodiment, this is done by associating suitable sensing means, such as a series of strain gauges 216 with the post 208, such as along each generally planar face thereof. Since the GRF of each foot during the leg extension exercise is transmitted to each end of the post 208, these strain gauges 216 provide a relative measure of the bilateral GRF, and thus may serve as a means for sensing a parameter of the exercise.

In terms of sensing parameters of the exercise, it may also be desirable to know the pedal angle during the exercise. This may be automatically estimated by measuring the relative angle of each boot 202a, 202b, such as by using a potentiometer or like means for sensing a parameter in order to determine relative position (e.g., the difference between a known or home position of the boot and the maximum position) during the exercise cycle. By comparing this measured pedal angle to a predetermined desired pedal angle, the stimulation can be adjusted accordingly (either manually or automatically, as described below) and help to ensure that the exercise is achieved in an even and desirable manner.

For purposes of adaptive control, it may also be necessary or desirable to measure the position of the sled 118 as a parameter of the exercise, which in turn may be used to determine its velocity during the exercise. As perhaps best understood with reference to FIGS. 3a and 3b, this may be easily accomplished using a rack 120 carried by the sled 118 for associating with a pinion 122 carried by the frame 114. An associated sensor or means for sensing, such as a potentiometer 124, detects the relative movement of the pinion 122 to assess the position of the sled from a known initial position, such as at the first end 114a of the frame 114.

Figure 6:
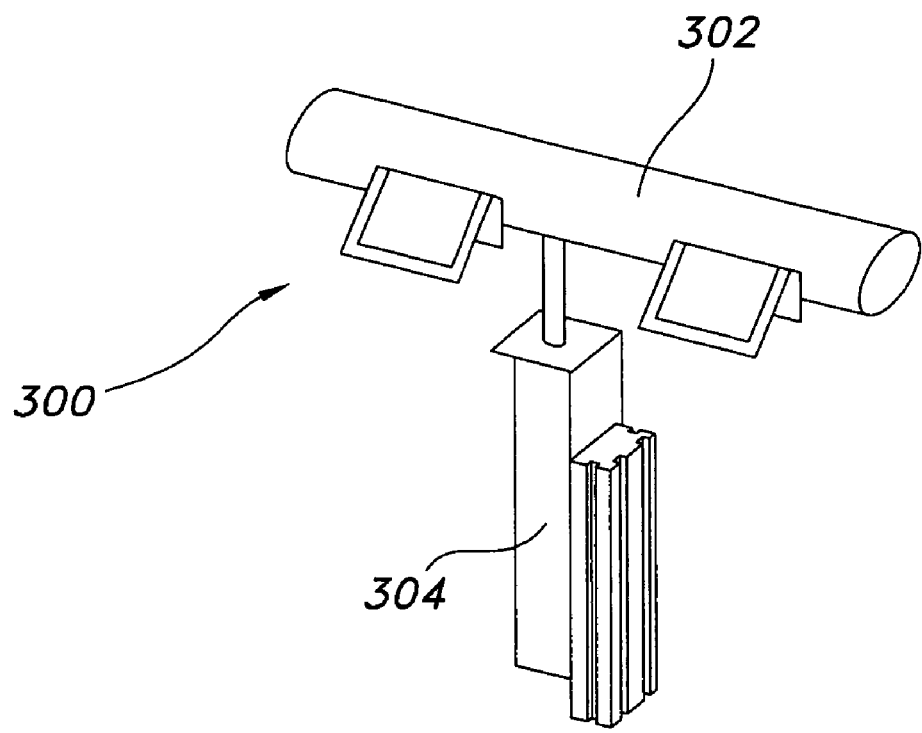
FIG. 6 is a perspective view of a knee flexion actuator.

With reference back to FIG. 2 and also to FIG. 6, the device 100 of this second embodiment may also include a knee flexion actuator 300, the purpose of which is to serve as a means for unbending the legs from the erect condition, usually once the second position is reached. This flexion actuator 300 in the illustrated embodiment includes a single cross bar 302 adapted for contacting the backs of the subject's knees. This cross bar 302 is in turn connected to an actuator, such as a linear actuator 304, oriented in a generally transverse direction. The linear actuator 304 is in turn mounted to a stable support structure, such as the frame 114 or frame extension 114c.

In use, the cross bar 302 is normally maintained in a retracted position, such that it lies adjacent to or contacts the backs of the subject's knees only when the legs are fully extended. At that point (which may be detected using the boot angle (or an average thereof), the sled position, the sled height in the vertical direction (which may be measured using an accelerometer), contact with the cross bar, or a combination thereof), the linear actuator 204 is activated to move the cross bar 302 into engagement with the then-adjacent back of the subject's knees with gentle, but sufficient force to "break" them from the locked condition or otherwise to facilitate the return of the legs to the bent condition such that the exercise may be repeated. The cross bar 302 may be immediately withdrawn and returned to the active position only upon completion of the next cycle of the leg extension exercise.

Figure 7:
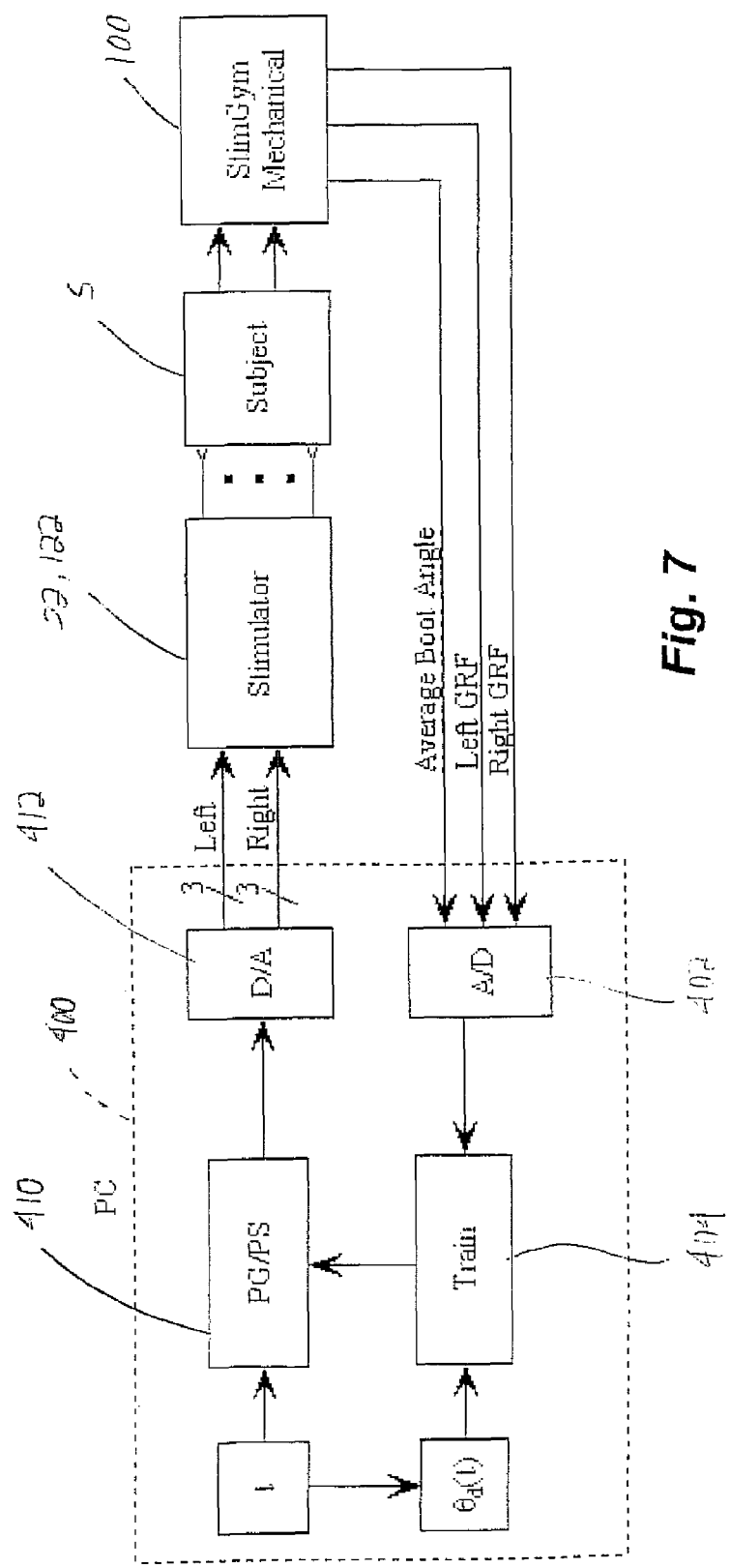
FIGS. 7-10a illustrate various aspects of one possible manner of controlling the exercise regimen.

With continued reference to FIG. 2a and reference also to the diagram of FIG. 7, control of the stimulator 122 associated with device 100 (or with stimulator 22 of device 10) during the exercise cycle may be manual, but is preferably autonomous using an associated controller forming part of a means for facilitating performance, such as by adjusting the level of stimulation. This controller may comprise software running on a personal computer 400 housed in an electronics enclosure E carried by or otherwise adjacent the base 112. This computer 400 may receive the sensed left and right ground reactive force (GRF) values and the actual sensed pedal, or "boot" angle as feedback, and then host and run one or more control algorithms for generating specific output signals to control the stimulator in real time to adapt (and preferably optimize) each successive cycle of the leg extension exercise.

Specifically, and as shown in FIG. 7, the output signals from the strain gauges and potentiometers measuring the boot angles (or the average boot angle) are converted if necessary using an analog-to-digital converter 402 and fed to a "training" algorithm 404. This training algorithm develops a rule by which to map "errors," or deviations in the measured values (e.g., boot angle and GRF), as well as in the velocity. The outputs of this training algorithm 404 may then be used in connection with pattern generating and pattern shaping/shaper (PGPS) algorithms (as described in detail in the following articles, which are again incorporated herein by reference: Reiss J, Abbas J J, *Adaptive Control of Cyclic Movements as Muscles Fatigue Using Functional Neuromuscular Stimulation*, IEEE Trans Neural Syst Rehabil Eng. 2001 September; 9(3): 326-30; Stites E C, Abbas J J, *Sensitivity and Versatility of an Adaptive System for Controlling Cyclic Movements Using Functional Neuromuscular Stimulation*, IEEE Trans Biomed Eng. 2000 September; 47(9): 1287-92; Reiss J, Abbas J J, *Adaptive Neural Network Control of Cyclic Movements Using Functional Neuromuscular Stimulation*, IEEE Trans Rehabil Eng. 2001 March; 8(1): 42-52; Abbas J J, Triolo R J, *Experimental Evaluation of an Adaptive Feedforward Controller for Use in Functional Neuromuscular Stimulation Systems*, IEEE Trans Rehabil Eng. 1997 March; 5(1): 12-22; and Abbas J J, Chizeck H J, *Neural Network Control of Functional Neuromuscular Stimulation Systems Computer Simulation Studies*, IEEE Trans Biomed Eng. 1995 November; 42(11): 1117-27) to adjust or revise the simulation level accordingly (including based on empirically determined constants, parameters, and pre-set stimulation maximums; see FIGS. 7, 7a, 8, 9a-9c, 10, and 10a, as well as the description that follows). Using such an adjustment means, a real-time, adaptive leg extension exercise can thus be achieved using the disclosed techniques, which although optional may greatly improve the quality of the exercise achieved.

Figure 8:
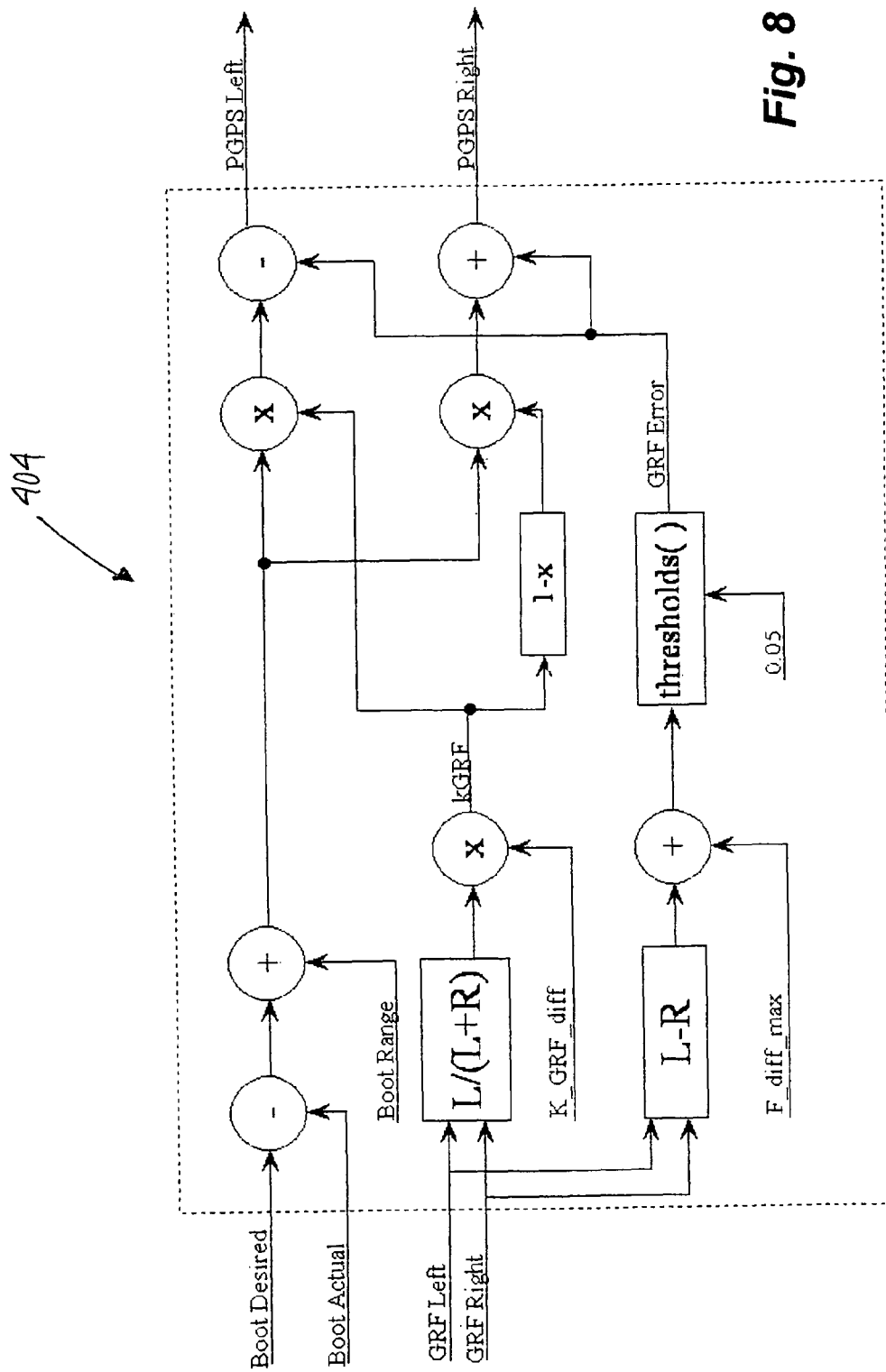
Figure 9A:
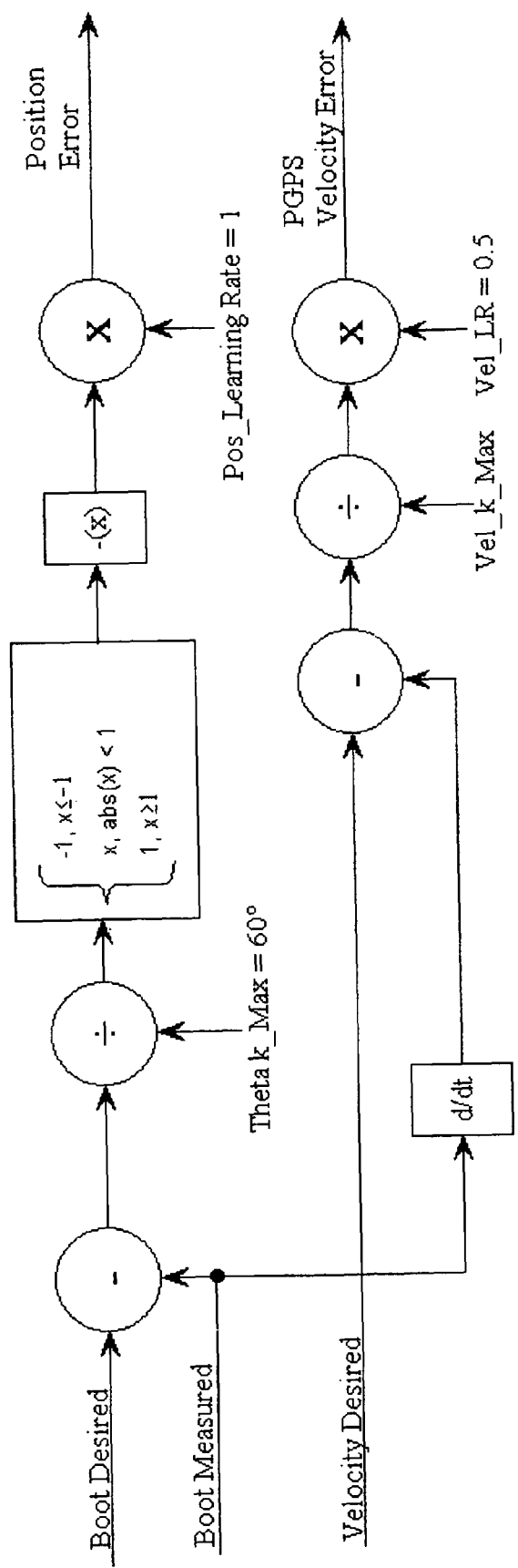

In the illustrated iteration, the training algorithm 404 is designed to determine a position error based on a predetermined desired pedal angle ($\theta_d$) and the actual pedal angle signal (such as that obtained from the associated potentiometer), balance the right and left GRFs as measured by the strain gauges, and also determine a velocity error based on the position error (FIGS. 8 and 9*a*). If the goal of the exercise is to perform it more slowly and thereby maximize the benefit while minimizing fatigue, as is typical, the desired velocity may be set at zero. Also, while the desired pedal angle ($\theta_d$) is predetermined and initially set at a large value, it may be adjusted accordingly to an actual, typically lower value once the subject performs the exercise and the actual range of motion is determined.

Figure 9B:
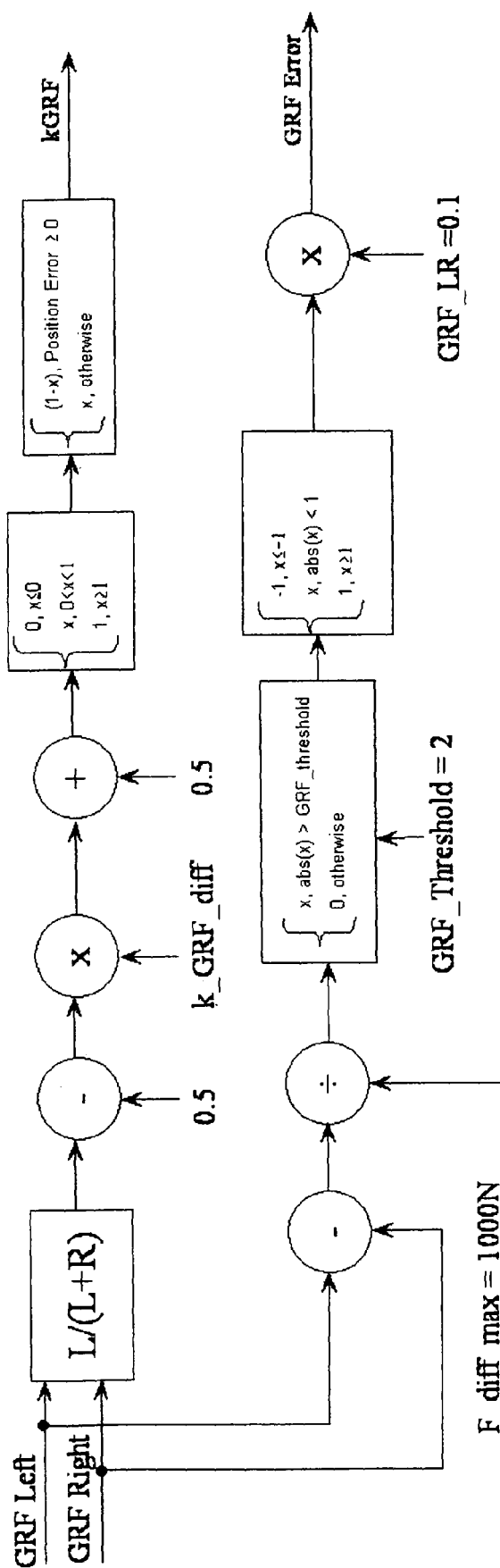
Figure 9C:
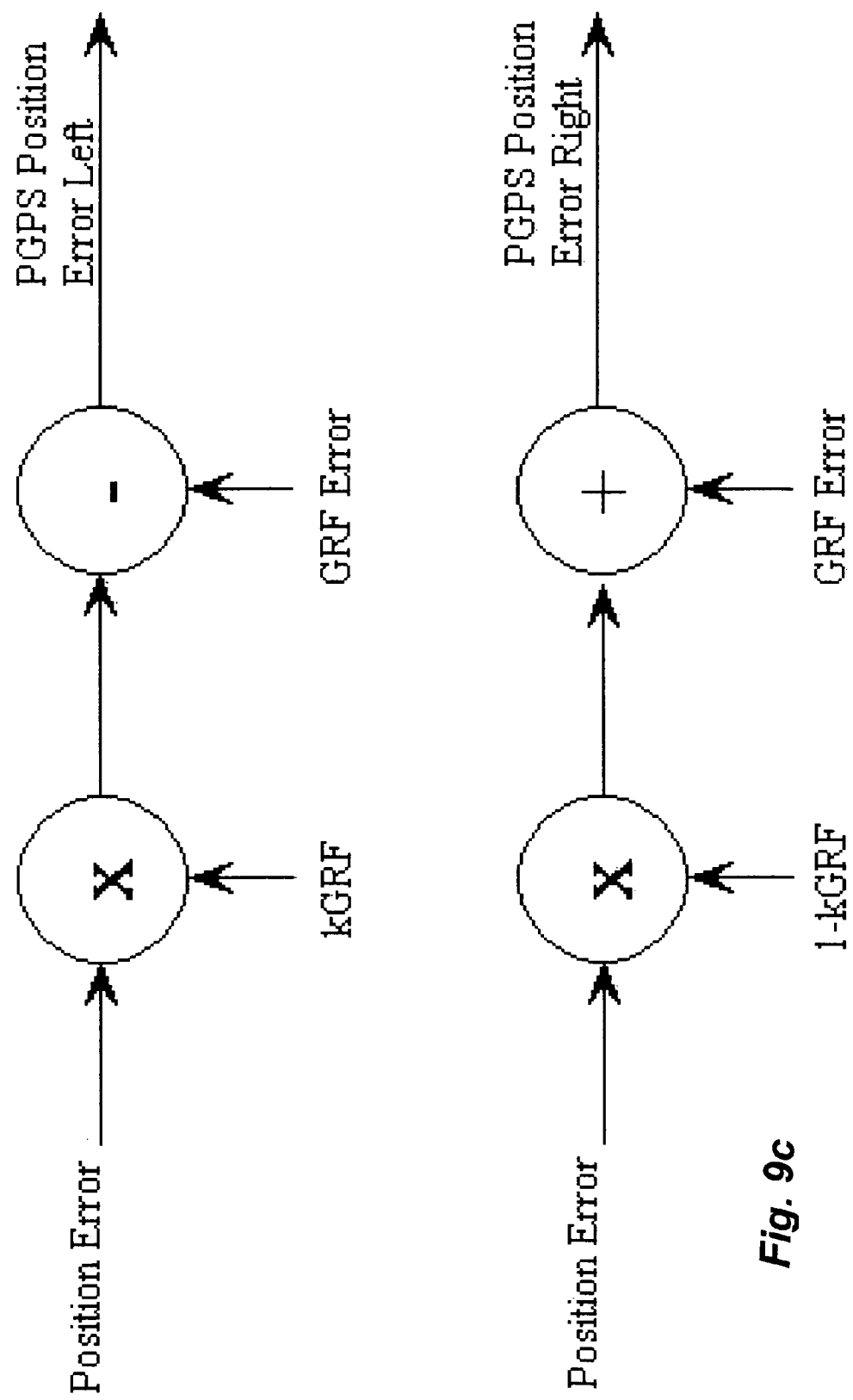

The right and left GRFs may be balanced using the algorithm shown in FIG. 9*b* and then used to calculate the left and right PGPS errors as shown in FIG. 9*c* and applied to the PGPS algorithm via the processing capabilities of the computer 400. Specifically, the left and right PGPS errors and velocity error are applied to corresponding PGPS controllers (labeled by a single block 410 within the computer 400) individually or independently (but may each be applied to a separate controller for the left and right sides). Regardless of the precise manner of production, the outputs from the PGPS controllers 410 are then converted back via converter 412 to the corresponding (left and right) analog signals (see FIG. 7). These signals are then used to adjust and drive the stimulator 22 to effect the desired stimulation of the extensor muscles in the upper leg of the subject S (but not the erector spinae muscles, which may simply be stimulated using a predetermined "ramp and hold" stimulation pattern) at a revised level and with adaptive feedback control based on one or more of the parameters sensed during the performance of the previous leg extension exercise.

Figure 10:
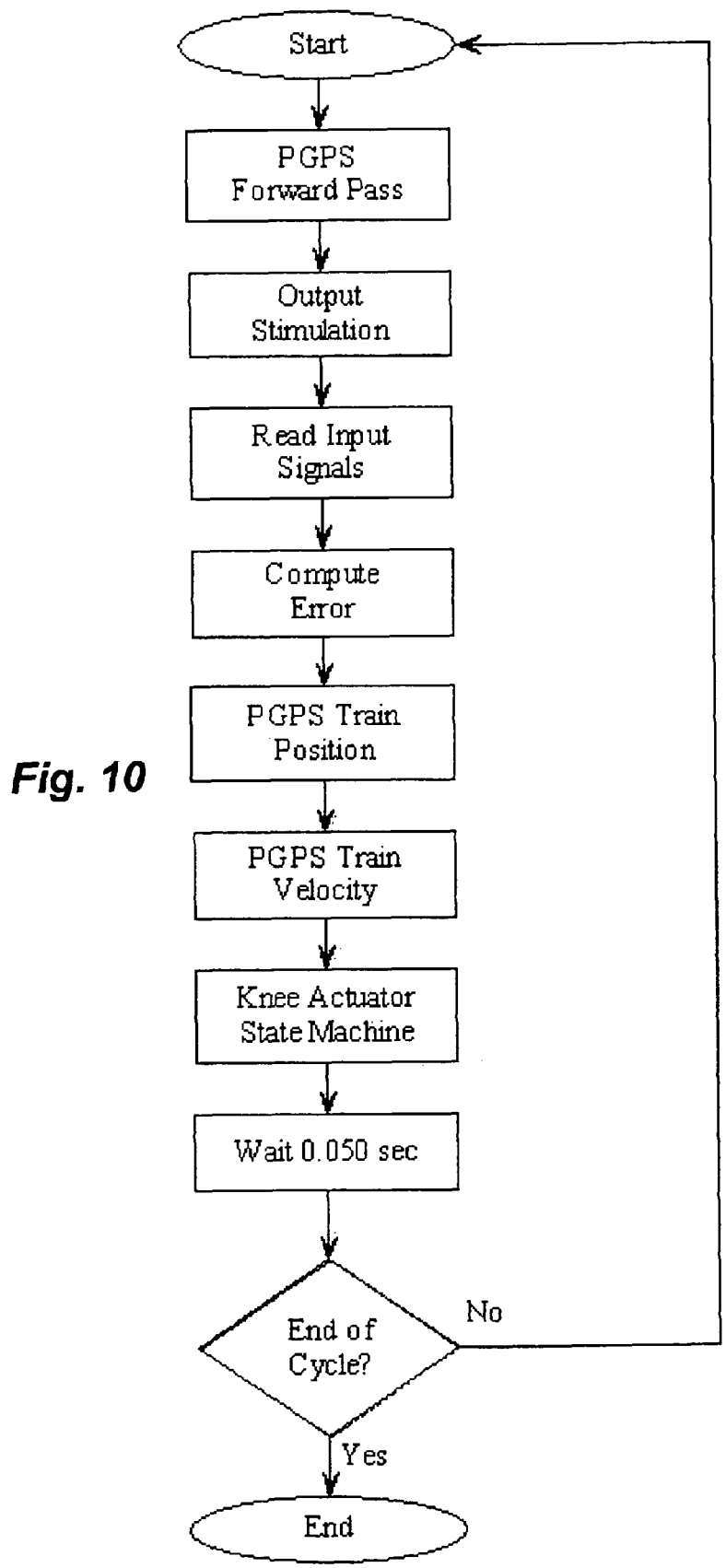
Figure 10A:
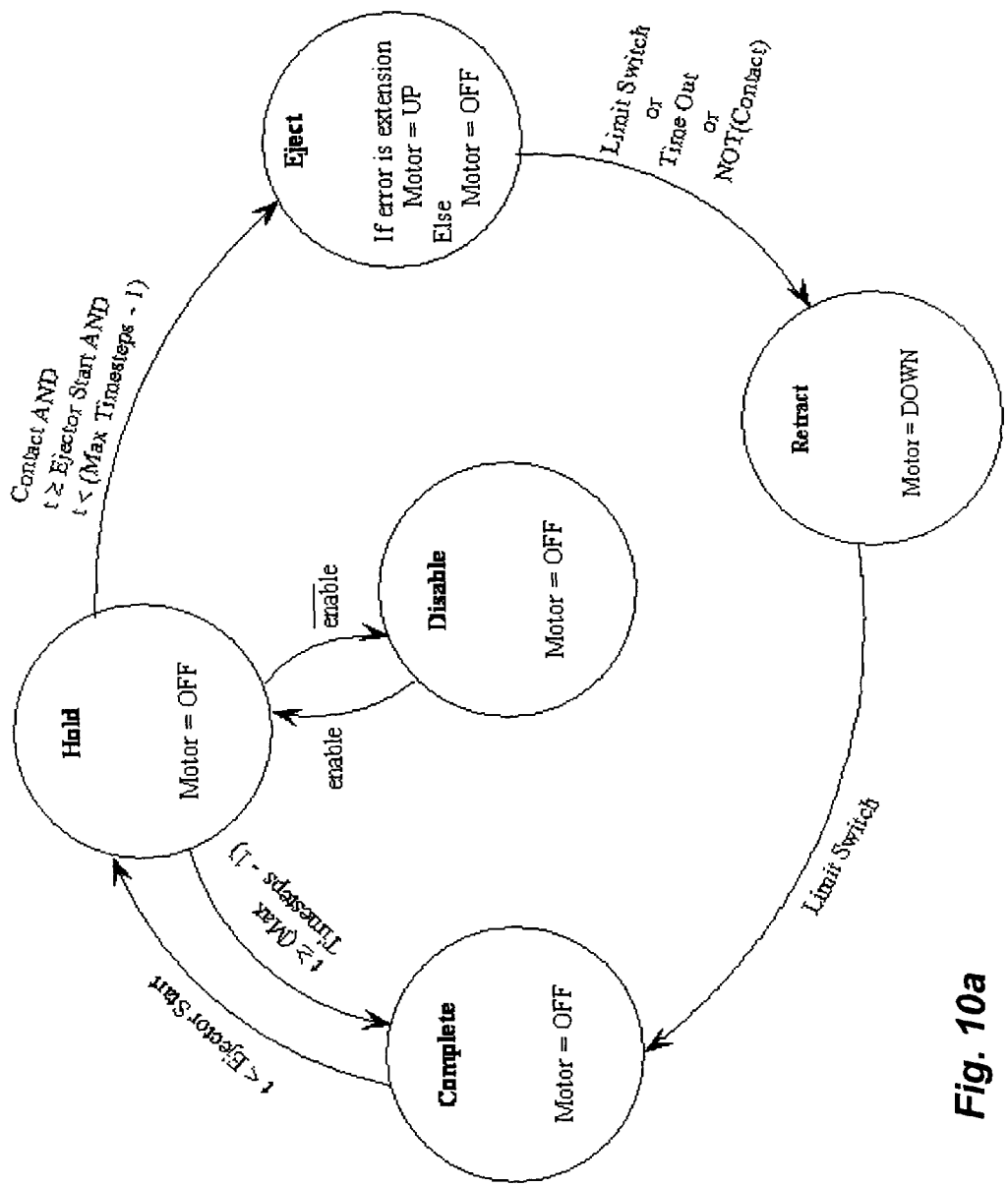
Figure 11A:
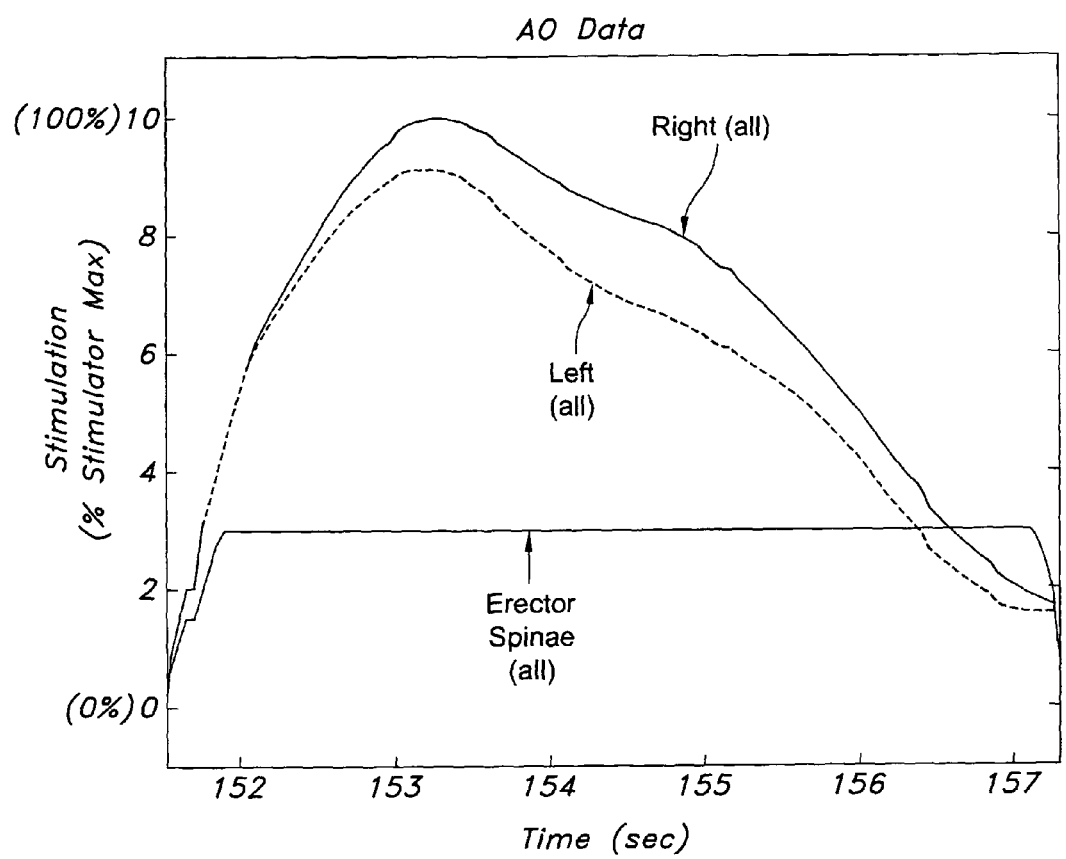
FIGS. 11a, 11b, and 11c are graphical depictions of various parameters of experimental exercise regimens.
Figure 11B:
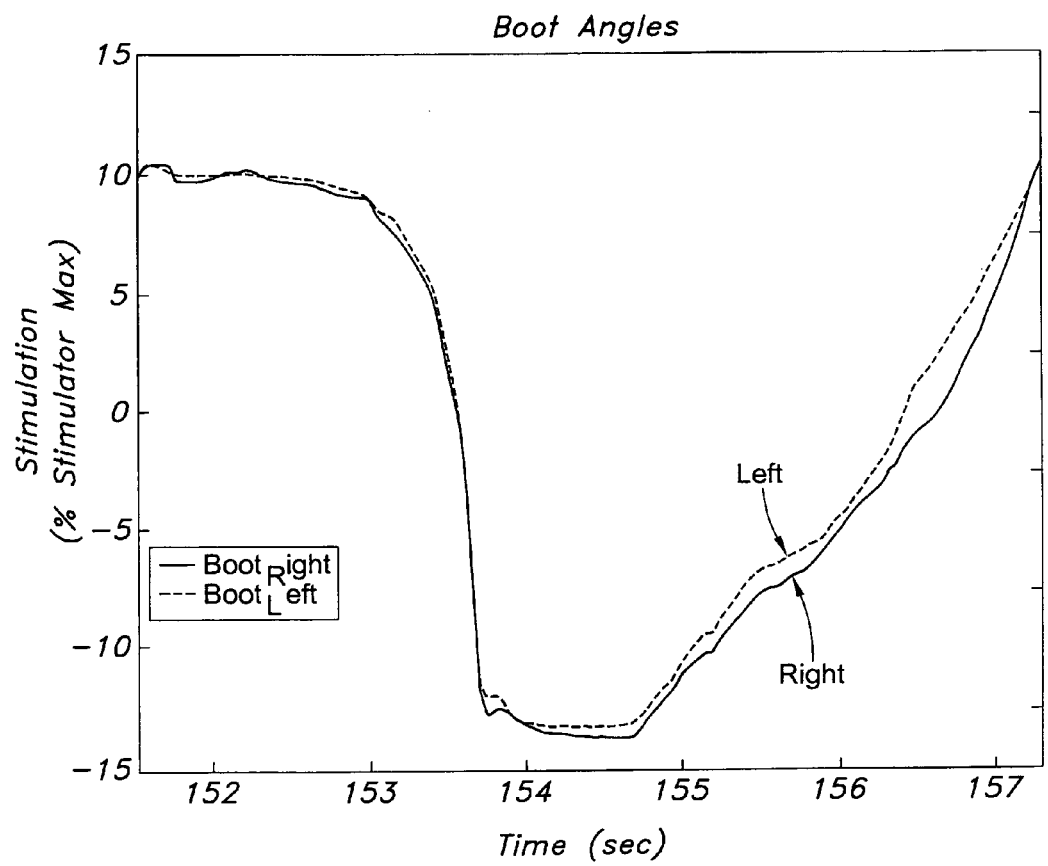
Figure 11C:
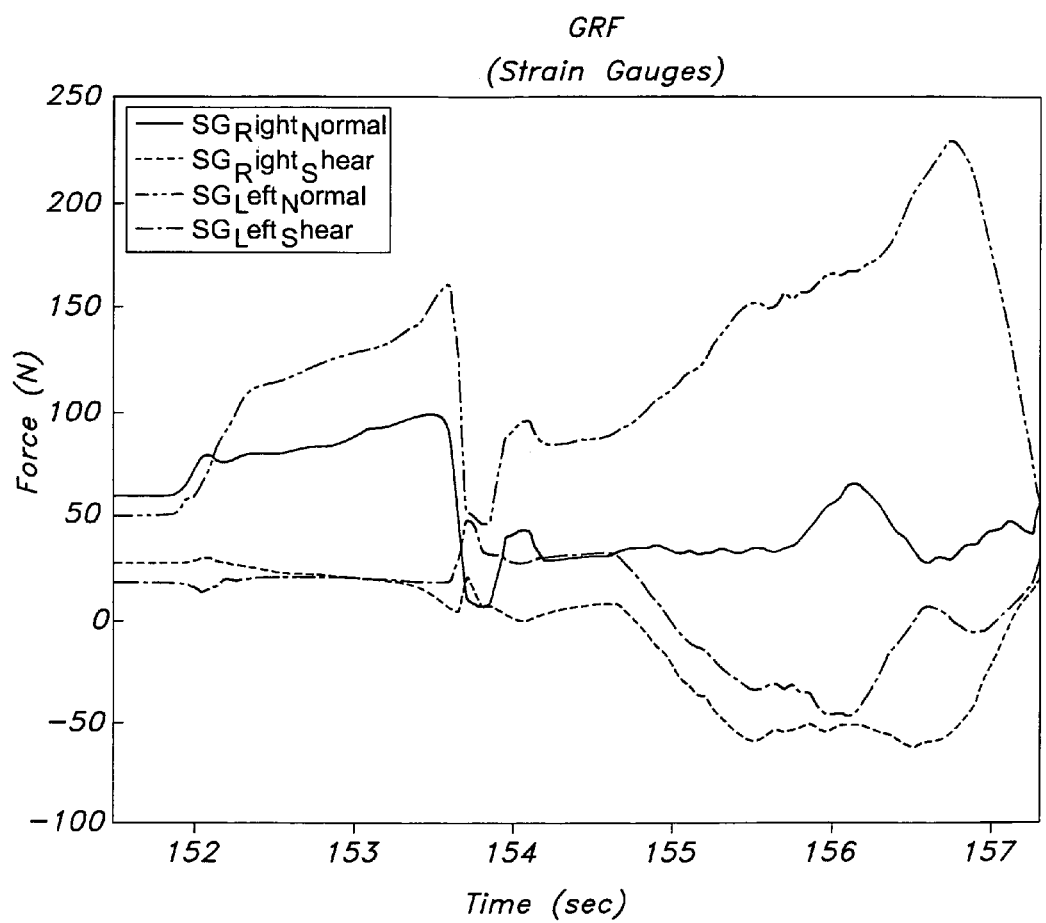

A flowchart showing a typical exercise cycle using the above-described adaptive feedback control algorithm is shown in FIG. 10, and with further reference to FIG. 10*a* for a state diagram showing the continuous nature of operation of the knee flexion actuator during the exercise (with the "error" being based on the difference between the desired boot angle and the measuring boot angle). Moreover, the stimulation levels, boot angles, and ground reactive forces during a single exercise cycle are shown in FIGS. 11*a*-11*c*. A typical cycle lasts 6 seconds followed by 2-4 seconds of rest. An exercise session may be composed of a strength protocol (4 sets of 10 exercise cycles separated by 5 minutes of rest) followed by an endurance protocol (100 exercise cycles). The exercise protocol may include intensity progressions based on performance in previous sessions. Intensity is varied by changing the knee angle range of motion (strength) and incline angle (endurance).

Starting, stopping, and monitoring of the exercise program may be accomplished though an input device associated with the controller, or computer 400, such as a touch display (not shown), keyboard and display unit, or the like. Likewise, the subject may have a separate or satellite display 502 for showing the specifics of the regimen, such as when to start and stop, as well as the rest period or delay between exercise periods. Subject and assistant-accessible emergency stop buttons (not shown) may also be provided to shut down the device 10, 100 immediately in the event a problem arises during the regimen.

Returning now to FIGS. 2*a* and 2*b*, still another embodiment of a closed-chain leg exercise device with stimulation for encouraging the subject's performance is shown. In this embodiment, the mechanical structure may be similar or identical to the device 100 shown, but could also be like the device 10 shown in FIG. 1. However, instead of applying electrical stimulation directly to the muscles through electrodes placed on the skin of the subject, sensory (e.g., visual) stimulation is provided in lieu of or in addition to electromuscular stimulation as a means of encouraging or facilitating performance of the exercise, such as by using a display device 502 or like graphical user interface (GUI) mounted within the view of the subject.

This display device 502 may display information to the subject regarding the parameters of the exercise, such as the amount of ground reactive force produced by each leg (which may be displayed as a "center-of-pressure" (i.e., the percentage of weight supported by each foot)). The subject may then adjust the exercise in an effort to equalize the forces, thus ensuring the desired even result (which can be especially important in situations where one of the legs is significantly stronger or more able than the other). The force levels or amounts may be displayed numerically, graphically (such as bars), or simply by a series of indicators (such as LEDs, buzzers, recorded words of encouragement, other visual or audible cues) that activate. Any like means of indicating or providing information regarding the ground reactive forces or the performance of the exercise generally could also be used for this purpose, without limitation.

In situations where the subject is not able to fully extend one or both of their legs, such as in the early days of rehabilitation after a stroke, the display 502 might instead show information regarding the position of the sled 118 as the legs move from the bent position, possibly along with a target position to be reached (which may be pre-set). This type of reinforcement or encouragement may be important in encouraging the subject to exercise and rewarding the performance, thus providing a sense of accomplishment.

Particular examples of various displays serving as possible graphical interfaces for the user (an exercise subject) are shown in FIGS. 12 and 13*a*-13*e*. FIG. 12 shows a display 600 presented to the subject in which a moving target 602 and a cursor 604 are provided. The target 602 and cursor 604 may move vertically in the middle of the display, with movement up corresponding to knee/hip extension and movement down corresponding to flexion. Preferably, the cursor 604 moves in a slow predicable pattern and the subject is instructed either visually or verbally to generate smooth, controlled exercise movement in an attempt to follow the target 602.

The subject may also attempt to perform the exercise movement while maintaining balanced left/right ground reaction forces, which are indicated by rotation of a crossbar 606 associated with the cursor 604. In the example display 600 shown, the target 606 moves up the display at a slow, steady pace. The subject is also moving the cursor 604 up the screen (extending his/her legs) and is correcting a balance shift (initially shifted to the right but being corrected). This visual display 600 is designed to emphasize sled movement over left/right balance.

FIG. 13*a* represents a display 700 associated with visually depicting the total amount of static force exerted during the exercise, such as in bar form. The associated exercise may require the subject, such as a stroke victim with partial immobility, to generate isometric force with their affected limb. This exercise preferably is performed at maximum sled incline angle and with the unaffected limb prevented from assisting with force generation.

FIG. 13*b* represents a display 800 associated with a "sit-to-stand" exercise that requires the subject to perform a simulated sit-to-stand transition and hold in the standing posture. Based on the sled position, the display 800 depicts the subject's body as an icon in at least the first and second positions.

FIG. 13c is a display 900 associated with an exercise designed to encourage the subject to perform weight shifts to their affected limb in the standing posture and hold it for a predetermined time (e.g., for 60 seconds). This task is designed to encourage the patient to partially support their bodyweight on the affected limb in preparation for standing. Weight distribution on the feet is used to determine the center of pressure in the mediolateral direction (COPML), which is displayed as a cursor 902 on the display 900. A target 904 also appears on the display 900 and the subject is instructed to adjust their balance from one foot to the other to place the cursor 902 in the target 904 and hold for a specified time. The target size is preferably large (size: 20%; limits: 80%-100%) to allow for variability in the early stages of rehabilitation. A premature transition to the resting posture may terminate the trial. Movement of the cursor 902 outside of the target 904 may also reset any associated timer.

FIG. 13d is a display 1000 that may be associated with a balanced sit-to-stand exercise. This task requires the subject to perform a balanced simulated sit-to-stand transition, and is designed to encourage patients to perform a coordinated movement using their affected and unaffected limbs. Sled position is visually represented by a cursor 1002, and mapped to vertical movement and COPML is mapped to horizontal movement. Subjects may then be instructed to keep the cursor 1002 inside the specified COPML range (indicated by vertical lines 1004, representing a range of ±10%) throughout the movement. On screen instructions may cue the user to "stand" or "sit". Subjects preferably are required to hold in the standing posture for a predetermine time (e.g., 30 seconds) before being instructed to return to the resting posture.

FIG. 13e is a display 1100 associated with an exercise requiring a subject to perform controlled dynamic balance shifts in the standing posture. The task is designed to encourage synergistic use of the affected and unaffected limbs to transfer and receive bodyweight in a controlled fashion as will be required for reaching tasks and gait. COPML may then be displayed as a cursor 1102 on the display 1100. A series of smaller targets 1104 (positions: ±25%, ±50%, size: 5%) sequentially appear on the display 1100, and the subject is instructed to adjust their balance to place the cursor 1102 in a selected target 1004 and hold for a predetermined time (e.g., 5 seconds). For example, a series of twelve targets may be presented in random order before returning to the resting posture. On screen instructions will cue the user to "sit" or "stand." Preferably, the targets 1104 do not appear on the screen until in the subject reaches the standing posture, and may change color when the cursor is within the target to indicate success.

As an alternative to the above, the blink rate of the cursor 1102 may be varied such that the ratio of on to off time will decrease from 1:1 to 0.2:1 (0.2 seconds ON followed by 1 second OFF) in a predetermined number of steps. To be successful, the subject must complete a predetermined number of sets (12 targets/set) at the 0.2:1 ratio within one session.

Another aspect of the invention is using the devices 10, 100 shown as a "tilt table" that allows a subject to exercise via knee/hip extension during tilt therapy. In such case, the "table" 10, 100 may be provided without the stimulation, and with a transfer height H of about 18 inches (FIG. 2b). A motorized incline 16 may also be provided to facilitate tilt adjustments. This offers a safe platform from which to perform closed-chain, load bearing knee extension exercises while minimizing the likelihood of falls, including with the application of partial bodyweight loading.

The foregoing descriptions of various embodiments of the invention are provided for purposes of illustration and not intended to be exhaustive or limiting. Modifications or variations are also possible in light of the above teachings. For example, the devices 10, 100 may be provided with locking wheels as shown in FIGS. 2a and 2b to facilitate movement over the ground. As noted above, it may also be desirable in some treatment regimens to combine the benefits of electrical stimulation with those of visual stimulation. Also, it may be desirable for the adjustment in the level of electrical stimulation to be manually performed by the exercise subject or an assistant based on the performance parameters. During the adaptive feed-forward control, the revised level of stimulation may also be identical or substantially identical to the previous level of stimulation based on the detected level of the corresponding exercise parameter. The embodiments described above were chosen to provide the best application to thereby enable one of ordinary skill in the art to utilize the disclosed inventions in various embodiments and with various modifications as are suited to the particular use contemplated. All such modifications and variations are within the scope of the invention.

The invention claimed is:

1. A device for performing a plurality of successive cycles of a closed-chain exercise with partial bodyweight loading for the lower extremities of a human subject including the legs, using stimulation, comprising:
    a frame;
    a sled for receiving the subject facing generally upwardly and mounted to the frame for translating from a first, lower position with the legs at least partially bent to a second, higher position with the legs less bent than in the first position;
    a pedal support for supporting at least one of the subject's feet, wherein the pedal support comprises a receiver mounted for moving as the sled moves from the first position to the second position, and a sensor for determining a relative position of the receiver during the exercise;
    an electrical stimulator for applying electrical stimulation to the human subject; and
    a controller for generating a plurality of output signals to control the stimulator during each exercise cycle to provide the electrical stimulation in an amount sufficient to cause the subject to move the sled from the first position toward the second position,
    whereby the stimulation provided may be automatically adapted by the controller for each successive cycle of the exercise.

2. The device according to claim 1, wherein the sled is slidably mounted to the frame, and further including a base for supporting the frame above the ground.

3. The device according to claim 1, further including a sensory stimulator for encouraging the subject to move the sled from the first position toward the second position.

4. The device according to claim 3, wherein the sensory stimulator includes a visual display for displaying information that encourages the subject to either balance or differ the force exerted by each leg.

5. The device according to claim 1, wherein an angle of the frame relative to a horizontal plane is adjustable.

6. The device according to claim 1, wherein the controller adjusts the electrical stimulation based on a sensed ground reactive force provided by the sensor associated with the pedal support.

7. The device according to claim 1, further including means for assisting in unbending the legs in the second position.

8. The device according to claim 1, wherein the plurality of output signals generated by the controller for a subsequent cycle of the exercise are based on a parameter of the exercise sensed during the performance of a previous cycle of the exercise.

9. The device according to claim 1, wherein the controller adjusts the electrical stimulation based on a sensed angle of the receiver.

10. The device according to claim 1, wherein the receiver comprises an elongated boot for receiving a portion of the subject's leg.

11. A device for facilitating performance of an exercise for the lower extremities of a human subject with partial or total loss of muscle control of the legs using stimulation and with the feet in contact with a stable support structure, comprising:
   an exercise sled for facilitating movement of the subject to and fro between a first position in which the legs are at least partially bent and a second position in which the legs are at least partially extended while the feet remain in contact with the stable support structure;
   a sensor for sensing a position of the subject between the first and second positions, wherein the sensed position relates to pedal angle;
   a sensory stimulator for providing stimulation based on the sensed position of the subject between the first and second positions; and
   an electrical stimulator for applying electrical stimulation to the human subject;
   whereby the stimulation provided based on the sensed position of the subject between the first and second positions helps to encourage the subject to voluntarily complete the exercise.

12. A method of performing a closed-chain leg extension exercise on a human subject with full or partial loss of leg muscle control, comprising:
   mechanically constraining at least a portion of the subject's lower leg;
   electrically stimulating at least a portion of the leg muscles at a predetermined level to move the legs between a first, bent position and a second, extended position during the closed-chain leg extension exercise;
   measuring an angle associated with the subject's leg;
   calculating a revised level of electrical stimulation comprising comparing the measured angle with a predetermined angle to determine a variation and determining the revised level based on the variation; and
   electrically stimulating at least a portion of the leg muscles at the revised level.

13. A method of performing a closed-chain leg extension exercise on a human subject with full or partial loss of leg muscle control, comprising:
   positioning the subject on a sled;
   electrically stimulating at least a portion of the leg muscles at a predetermined level to move the legs between a first, bent position and a second, extended position during the closed-chain leg extension exercise;
   detecting a velocity error signal;
   calculating a revised level of electrical stimulation based on the velocity error signal; and
   electrically stimulating at least a portion of the leg muscles at the revised level.

* * * * *

UNITED STATES PATENT AND TRADEMARK OFFICE
CERTIFICATE OF CORRECTION

PATENT NO. : 8,249,714 B1  
APPLICATION NO. : 11/483786  
DATED : August 21, 2012  
INVENTOR(S) : Eric Hartman et al.

Page 1 of 1

It is certified that error appears in the above-identified patent and that said Letters Patent is hereby corrected as shown below:

Column 1, line 10, in the GOVERNMENT RIGHTS, please replace "Certain aspects of the disclosed inventions were made with support under grants from the National Institutes of Health, National Institute of Child Health and Development, and the National Center for Medical Rehabilitation Research (Grant Nos. NIH-NICHD NCMRR 1-R43-HD39013, NIH-NICHD NCMRR 1-R44-HD39013, and NIH-NINDS 1-R43-NSO45448). The government may have certain rights in this invention."

with:

-- This invention was made with government support under NIH-NICHD NCMRR 1-R43-HD39013 awarded by National Institute of Health. The government has certain rights in the invention.

This invention was made with government support under NIH-NICHD NCMRR 1-R44-HD39013 awarded by National Institute of Child Health and Development. The government has certain rights in the invention.

This invention was made with government support under NIH-NINDS 1-R43-NOS45448 awarded by National Center for Medical Rehabilitation Research. The government has certain rights in the invention. --

Signed and Sealed this  
Twenty-sixth Day of February, 2013

Teresa Stanek Rea  
*Acting Director of the United States Patent and Trademark Office*